(12) United States Patent
Akers et al.

(10) Patent No.: US 7,390,653 B2
(45) Date of Patent: *Jun. 24, 2008

(54) CULTURE CHAMBER FOR BIOLOGICALS

(75) Inventors: Roger Akers, Houston, TX (US); William J. Anderson, Richmond, TX (US); Adrian F. Dinges, Jr., Houston, TX (US); Stephen S. Navran, Jr., Houston, TX (US)

(73) Assignee: Synthecon, Inc., Houston, TX (US)

( * ) Notice: Subject to any disclaimer, the term of this patent is extended or adjusted under 35 U.S.C. 154(b) by 706 days.

This patent is subject to a terminal disclaimer.

(21) Appl. No.: 10/725,607

(22) Filed: Dec. 2, 2003

(65) Prior Publication Data

US 2004/0110273 A1 Jun. 10, 2004

Related U.S. Application Data

(60) Provisional application No. 60/430,795, filed on Dec. 4, 2002.

(51) Int. Cl.
*C12M 1/00* (2006.01)
*C12M 3/00* (2006.01)
*C12M 1/12* (2006.01)
*C12M 1/14* (2006.01)
*C12M 3/04* (2006.01)
*B01D 63/00* (2006.01)
*C02F 1/44* (2006.01)

(52) U.S. Cl. ............... 435/297.2; 435/295.3; 435/297.3; 435/298.1; 435/299.1; 435/304.1; 210/321.6; 210/321.87; 210/321.89; 210/321.78

(58) Field of Classification Search ............. 435/297.2, 435/289.1, 295.3, 297.3, 298.1, 299.1, 304.1; 210/321.6, 321.87, 321.89, 321.78
See application file for complete search history.

(56) References Cited

U.S. PATENT DOCUMENTS

| | | | |
|---|---|---|---|
| 3,682,318 A * | 8/1972 | Rigopulos | 210/321.87 |
| 3,722,694 A * | 3/1973 | Agranat | 210/321.89 |
| 4,988,623 A | 1/1991 | Schwartz et al. | |
| 5,026,650 A | 6/1991 | Schwartz et al. | |
| 5,104,802 A | 4/1992 | Rhodes et al. | |
| 5,153,131 A | 10/1992 | Wolf et al. | |
| 5,153,133 A | 10/1992 | Schwartz et al. | |
| 5,155,034 A | 10/1992 | Wolf et al. | |
| 5,155,035 A | 10/1992 | Schwartz et al. | |

(Continued)

OTHER PUBLICATIONS

Rai M. et al.; Expression systems for production of heterologous proteins, Current Science, vol. 80, No. 9, May 10, 2001, pp. 1121-1128.

(Continued)

*Primary Examiner*—William H. Beisner
*Assistant Examiner*—Nathan A Bowers
(74) *Attorney, Agent, or Firm*—Elizabeth R. Hall

(57) ABSTRACT

The culture chamber of the present invention has a fluid-filled culture compartment in which cells, tissues and other biologicals are cultured. The culture compartment is transversed by one or more molecular weight cut-off membranes attached to a membrane carrier assembly. Incoming nutrients are transported through the membrane into the culture compartment and metabolic waste products are transported away from the fluid-filled culture compartment through the membrane and out the chamber outlet. Both reusable and disposable culture chambers are described for culturing cells, cell aggregates, particles, tissues and organoids.

8 Claims, 15 Drawing Sheets

U.S. PATENT DOCUMENTS

| | | |
|---|---|---|
| 5,449,617 A | 9/1995 | Falkenberg et al. |
| 5,576,211 A * | 11/1996 | Falkenberg et al. ...... 435/297.1 |
| 5,637,477 A | 6/1997 | Spaulding et al. |
| 5,686,301 A | 11/1997 | Falkenberg et al. |
| 5,998,202 A | 12/1999 | Schwartz et al. |
| 6,022,733 A | 2/2000 | Tam et al. |
| 6,080,581 A | 6/2000 | Anderson et al. |
| 6,107,055 A * | 8/2000 | Bauer et al. ................ 435/68.1 |
| 6,228,607 B1 * | 5/2001 | Kersten et al. ................ 435/41 |

OTHER PUBLICATIONS

Verma, R. et al.; Antibody engineering: Comparison of bacterial, yeast, insect and mammalian expression systems, Journal of Immunological Methods, 216, 1998, pp. 165-181.

Hernaeus Instruments, Inc.; Genetic Engineering News, vol. 14, No. 12, Jun. 15, 1994.

FiberCell Hollow Fiber Cell Culture Systems, Dec. 1, 2004 printout, Internet at bellcoglass.com.

* cited by examiner

CULTURE CHAMBER FOR BIOLOGICALS

CROSS REFERENCE TO RELATED APPLICATIONS

This application claims priority to U.S. Patent Application Ser. No. 60/430,795 filed Dec. 4, 2002 by inventors Roger Akers, William Anderson, Steve Navran and Adrian Dinges and entitled "Culture Vessels for Biologicals." The entire text of the above-referenced disclosure is incorporated by reference herein.

BACKGROUND OF THE INVENTION

1. Field of the Invention

The present invention relates to a culture chamber for culturing cells, cellular aggregates, particles, tissues and organoids. More particularly, the present invention relates to a culture chamber having one or more molecular weight cut-off membranes transversing the chamber, wherein incoming media enters the chamber through an inlet and then passes through a membrane into the culture chamber and the exiting media passes through the membrane and then out the chamber outlet.

2. Description of the Related Art

The biomanufacturing industry is experiencing rapid growth. One aspect of that growth is that the demand for the production of new therapeutic protein products is greatly exceeding capacity. To keep pace with the drugs and antibodies generated in cell culture that are coming to market, biomanufacturing industry requirements for therapeutic protein production is expected to increase yet another five or six fold over the next couple of years. Since the industry is already exceeding current capacity for the production of therapeutic proteins, new processes and apparatuses are needed that are more efficient and that can be scaled up for the production of larger quantities of therapeutic proteins.

One of the major problems in producing therapeutic protein products is the time and costs of purifying the desired protein from the cell media. It is estimated that two thirds of the time and costs of manufacturing proteins from cell cultures is related to the separation of the desired protein product from the waste products. Thus, there is a need to produce a more concentrated protein product upstream to reduce the downstream processing required to purify the protein product.

In addition, the expense of producing biologicals in aseptic bioreactors is exacerbated by the required cleaning, sterilization and validation of the standard stainless steel or glass bioreactors by the customer. There is a continuing need to develop lightweight, presterilized, disposable culture chambers with simple connections to existing equipment that require little training to operate, yet provide the necessary gas transfer and nutrient mixing required for successful cell cultures. If the culture chambers used in producing therapeutic proteins could be made disposable, a reduction in the risk of cross contamination, the time and expense in changing from the production of one protein to another, and the downtime needed for equipment changeover between production runs would be realized.

SUMMARY OF THE INVENTION

The invention contemplates a culture chamber having a fluid-filled compartment in which cells, tissues and other biologicals are cultured. The culture chamber is transversed by one or more molecular weight cut-off membranes. Incoming nutrients are transported through the membrane into the culture chamber and metabolic waste products are transported away from the fluid-filled culture compartment through the membrane and out the chamber outlet.

One aspect of the present invention is a culture chamber comprising: a tubular housing; a growth compartment within the housing; a fluid inlet; a fluid outlet; and a membrane carrier assembly transversing the growth compartment including a support cylinder having a first end in communication with the fluid inlet and a second end in communication with the fluid outlet, a molecular weight cut-off membrane secured to an exterior surface of the support cylinder, and a chamber between the exterior surface of the cylinder and an interior surface of the membrane, the chamber in fluid communication with the fluid inlet and the fluid outlet.

Another aspect of the present invention is a culture vessel comprising: (a) a housing having a right circular cylindrical sleeve having a first and a second end; and a first and a second end fitting including an interior projection, the interior projection having an outer diameter that sealingly fits within a bore of the sleeve to seal the first and second ends of the sleeve, a nozzle on an exterior side of the end fitting, a counterbore in the interior projection, and a through bore passing through the end fitting, the through bore extending from the nozzle to the counterbore; (b) a growth compartment within the bore of the sleeve; (c) a support cylinder transversing the growth compartment, the support cylinder having a first and second end, each end having a fluid channel extending from the end of the cylinder to an exterior surface of the cylinder in a mid-section of the cylinder, wherein the fluid channel is in communication with the through bore of the end fitting whenever the cylinder is positioned in the counterbore of the interior projection; and (d) a molecular weight cut-off membrane secured to an exterior surface of the support cylinder to provide a chamber between the exterior surface of the cylinder and an interior surface of the membrane, the chamber in fluid communication with the fluid channels of the support cylinder.

Another aspect of the present invention is a disposable culture bag comprising: (a) a flexible outer wall having a first end, a second end, an internal side, and an external side, wherein the internal side of the wall is positioned to face an interior of the culture bag; (b) an inlet means fused to the first end of the wall, wherein the inlet means includes an inlet end piece having an inlet interior counterbore and an inlet through bore; (c) an outlet means fused to the second end of the wall, wherein the outlet means includes an outlet end piece having an outlet interior counterbore and an outlet through bore; and (d) a membrane carrier assembly connecting the inlet through bore to the outlet through bore including a support cylinder positioned at a first end in the inlet interior counterbore and at a second end in the outlet interior counterbore, the support cylinder having a fluid channel at the first end and second ends in communication with the inlet and outlet through bores, a molecular weight cut-off membrane secured to an exterior surface of the support cylinder, and a chamber between the exterior surface of the cylinder and an interior surface of the membrane, the chamber in fluid communication with the inlet and outlet through bores.

Yet another aspect of the present invention is a method of culturing cells in a culture chamber having a growth compartment transversed by a support cylinder surrounded by a molecular weight cut-off membrane to form a fluid chamber between the support cylinder and the membrane, the fluid chamber in fluid communication with a fluid inlet and a fluid outlet, the method comprising the steps of: (a) filling the growth compartment with a nutrient media; (b) placing a cell culture mixture in the nutrient media in the growth compartment; (c) rotating the culture chamber; (d) pumping additional nutrient media into the fluid inlet, through the fluid chamber, and out the fluid outlet; and (e) transporting a number of compounds having a molecular weight less than the molecular weight cut-off of the membrane across the membrane.

The foregoing has outlined several aspects of the present invention in order that the detailed description of the invention that follows may be better understood. Additional features and advantages of the invention will be described hereinafter which form the subject of the claims of the invention. It should be appreciated by those skilled in the art that the conception and the specific embodiments disclosed might be readily utilized as a basis for modifying or redesigning the method or process for carrying out the same purposes as the invention. It should be realized that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

DESCRIPTION OF THE PREFERRED EMBODIMENTS

The culture chamber of the present invention has a culture compartment in which cells, tissues and other biologicals are cultured in fluid media. The culture compartment is transversed by one or more molecular weight cut-off membranes attached to a membrane carrier assembly. Incoming nutrients and/or biological modifiers are transported through the membrane into the culture compartment and metabolic waste products are transported away from the fluid-filled culture compartment through the membrane and out the chamber outlet. Both reusable and disposable culture chambers are described for culturing cells, cell aggregates, particles, tissues and organoids.

The molecular weight cut-off membranes that transverse the culture compartment permit two-way perfusion into and out of the cell growth chamber. The membranes allow nutrients, growth factors and gases in the input fluid entering through the inlet means of the culture chamber to perfuse into and throughout the interior of the culture compartment. At the same time waste products are able to perfuse out of the chamber through the molecular weight cut-off membrane in the reverse direction into the exiting fluid that passes through the interior of the membrane. The use of multiple membranes transversing the culture compartment ensures that fluid entering through the inlet means of the culture chamber perfuses throughout the interior of the culture compartment and is well mixed with the media within the culture compartment. The culture chambers of the present invention include both reusable chambers and chambers having a reusable housing containing a disposable bioreactor bag.

Figure 1:
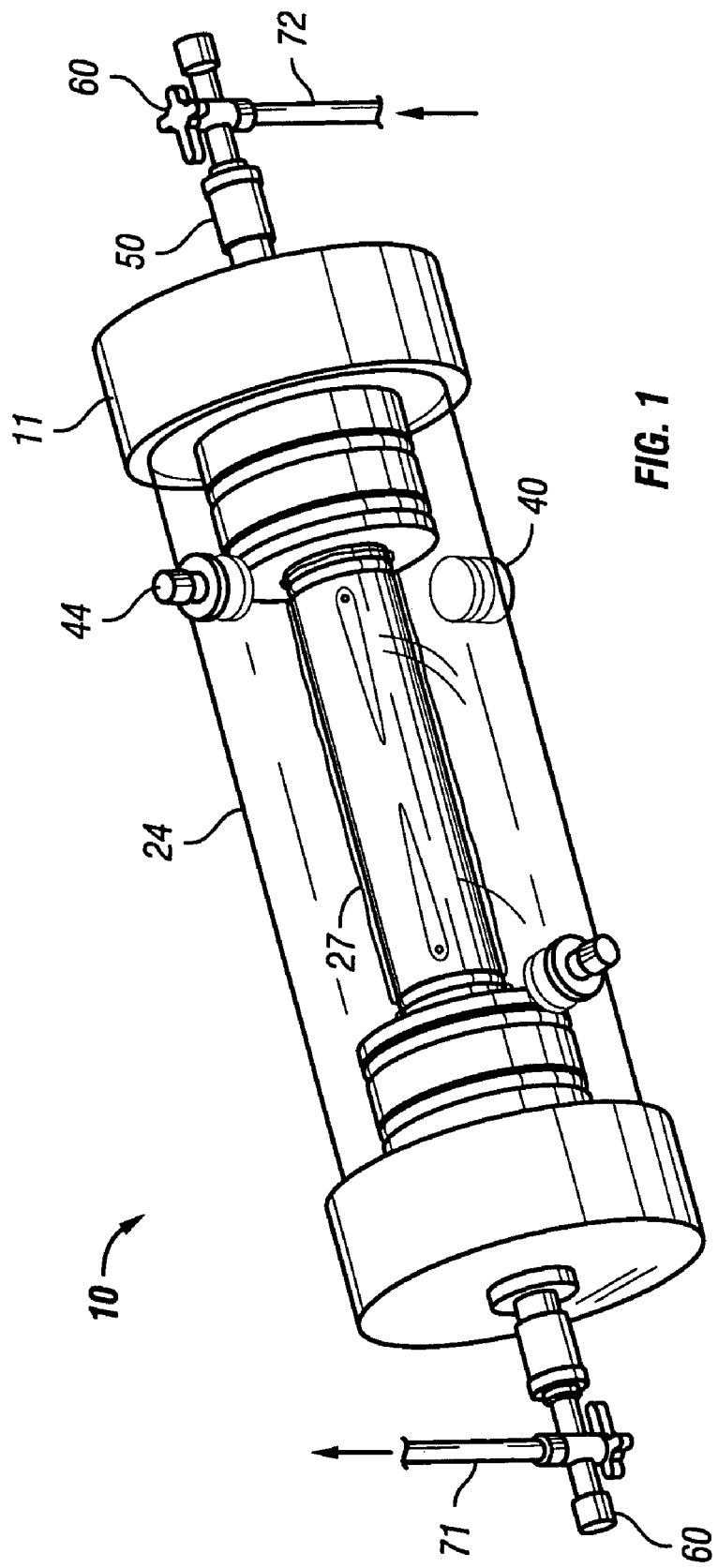
FIG. 1 shows an oblique view of the one embodiment of the present invention of a cell culture chamber utilizing a molecular weight cut-off membrane.

Referring now to the drawings, and initially to FIG. 1, it is pointed out that like reference characters designate like or similar parts throughout the drawings. The Figures, or drawings, are not intended to be to scale. For example, purely for the sake of greater clarity in the drawings, wall thickness and spacing are not dimensioned as they actually exist in the assembled embodiment.

Reusable Culture Chambers

Figure 2:
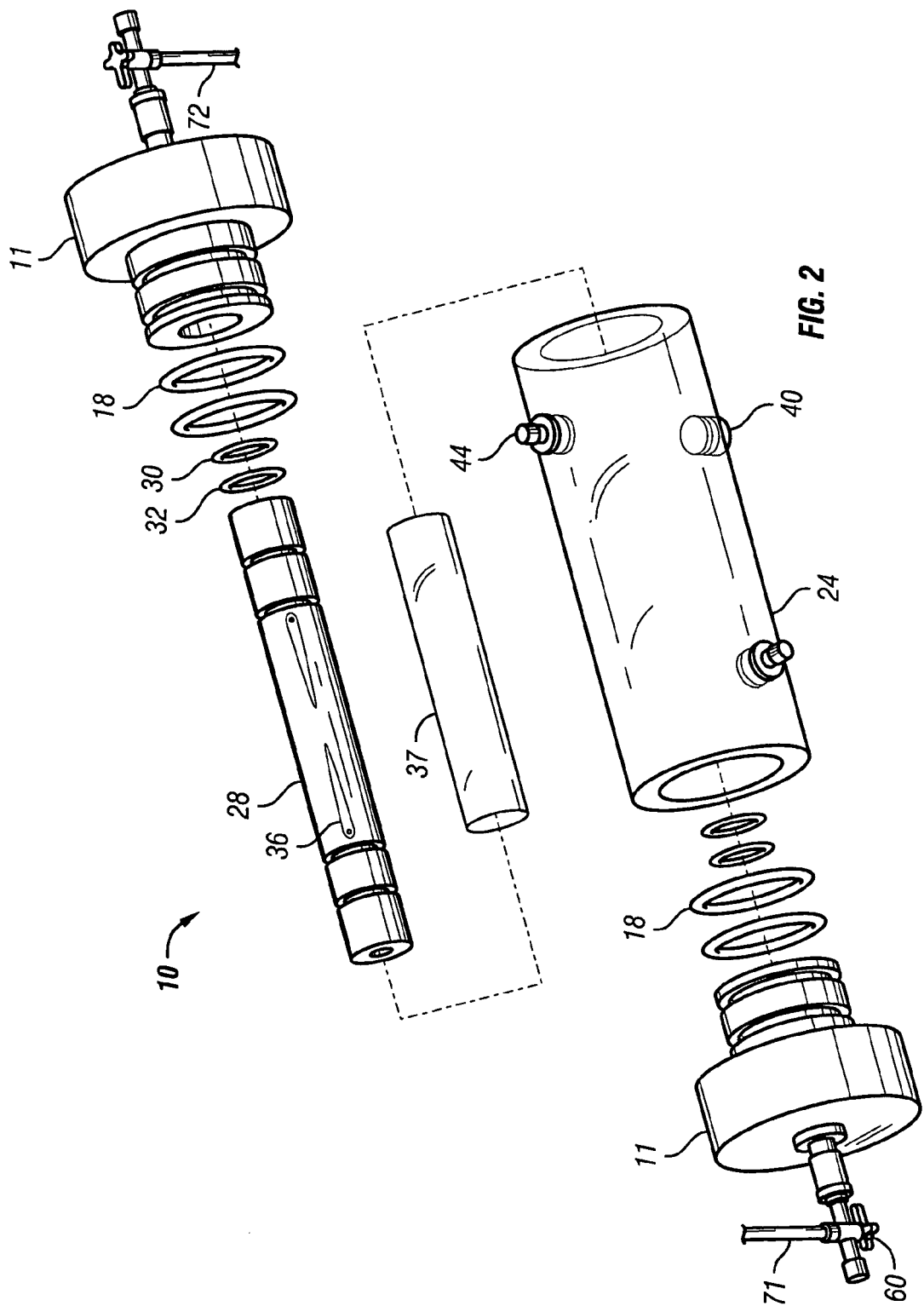
FIG. 2 shows an exploded oblique view of the cell culture chamber of FIG. 1.
Figure 3:
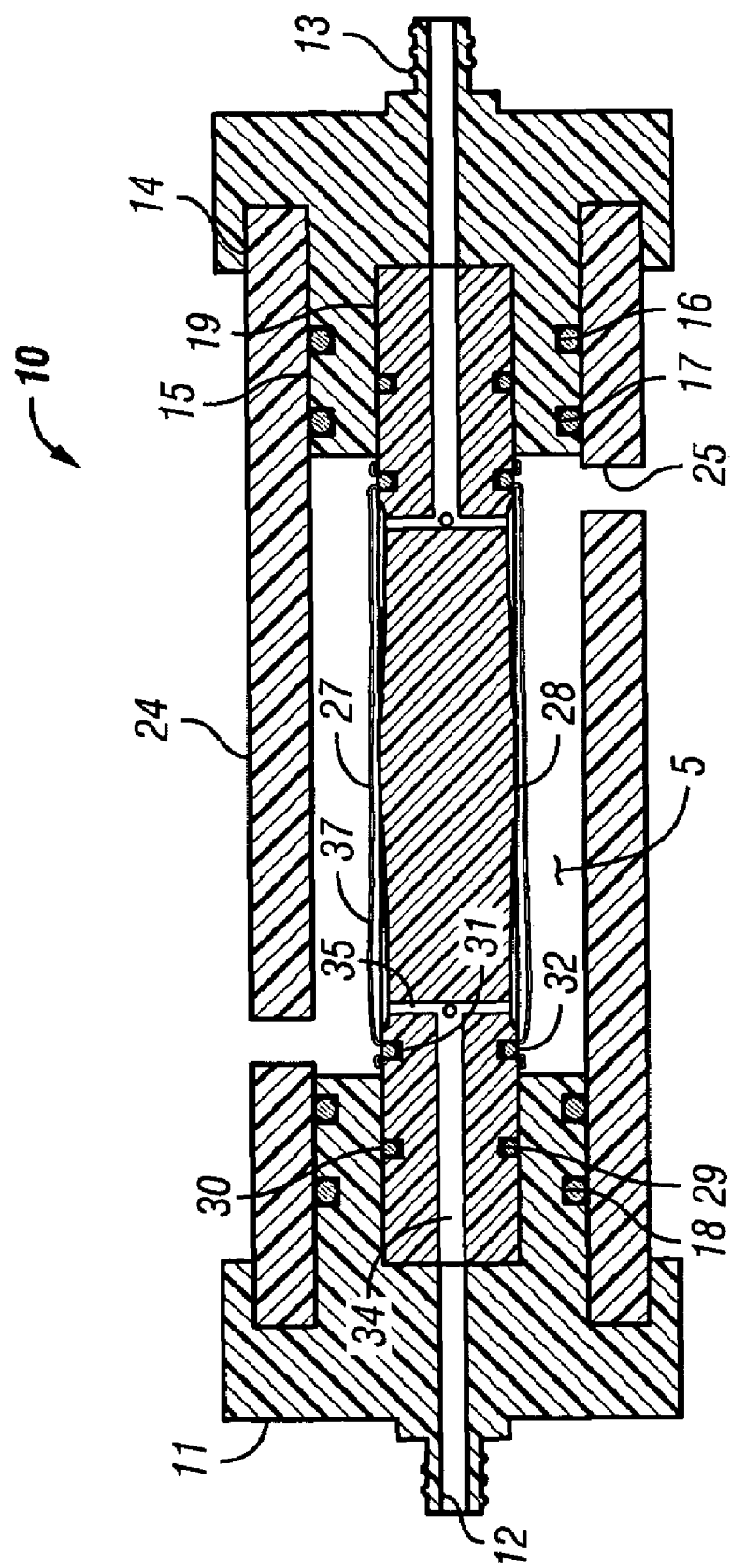
FIG. 3 shows a longitudinal cross-sectional view of the cell culture chamber of FIG. 1 with the end swivels and shutoff valves removed.

FIG. 1 shows one embodiment of a reusable culture chamber 10. As shown in FIGS. 1-3, two identical end pieces 11 seal to the ends of right circular cylindrical tubular sleeve 24 so that a growth compartment 5 is formed within the enclosed space. When in use for culturing cells, cellular aggregates, particles, tissues and organoids, the culture chamber is designed to be supported on and rotated by a roller drive which rotates the chamber about its axis. A variety of drive assemblies may be used to rotate the culture chamber such as the drive assembly described in U.S. Pat. No. 6,080,581.

The biologicals being cultured in the rotatable chamber require nutrients, so fluid-conducting swivels 50, stopcock valves 60, and fluid inlet tubing 72 and outlet tubing 71 are provided on the ends of the housing 10 so that the entry and exit of media is controlled. Multiple radial wall penetration ports 25 are provided in the annular wall of sleeve 24 to allow the introduction of one or more fill ports 40 and one or more vent ports 44. The swivel 50, the fill port 40, and the vent port 44 are described in more detail below.

The particulars of the construction of the components of culture chamber 10 are best understood with reference to FIGS. 1-4. End piece 11 has a right circular cylindrical central body having a coaxial push-on hose barb attachment neck 13 on its outer face. Axial through hole 12 penetrates through attachment neck and the rest of the body of end piece 11. Reduced diameter coaxial right circular cylindrical interior projection 15 extends inwardly on the transverse face of the interior end of end piece 11, with a flat-bottomed trepanned groove 14 located on the transverse interior face of end piece 11 immediately exterior of projection 15. The exterior cylindrical surface of interior projection 15 has, in order from the interior transverse face of end piece 11, first and second annular male O-ring grooves 17 and 16. Elastomeric O-rings 18 are mounted in O-ring grooves 16 and 17. At the interior end of interior projection 15 of end piece 11, flat-bottomed coaxial counterbore 19 intersects through hole 12. An optional lead-in chamfer may be provided at the mouth of counterbore 19 in order to facilitate the stabbing of an O-ring seal with the membrane carrier assembly.

The right circular cylindrical sleeve 24 can be made of a variety of materials such as glass, stainless steel or plastic. Preferably the reusable cell culture chamber is constructed of plastic, typically a transparent plastic such as an acrylic plastic for the cylindrical sleeve 24 and opaque plastics such as Kynar™ or Delrin™ for the other rigid pieces such as the end pieces 11. Suitable plastics have substantially zero porosity and are impermeable to gases and non-reactive to biological media and its components. Suitable construction materials must also be able to undergo multiple sterilizations by steam, gas, or radiation without deforming, cracking or otherwise being rendered unusable.

Although not shown in FIG. 3, the right circular cylindrical sleeve 24 is preferably provided with a lead-in taper on each of its interior corners to facilitate the stabbing of O-rings. The interior bore of sleeve 24 is a close sliding fit to the outer diameter of interior projection 15 of end fitting 11, thereby permitting O-rings 18 in the O-ring grooves 16 and 17 to sealingly engage the bore of sleeve 24. As stated previously, the sleeve 24 has multiple radial wall penetration ports 25 to allow the mounting of fittings used for inserting fluid into or removing fluids from the growth compartment 5 and for allowing gas to escape from the growth compartment 5 as it is being filled with fluid. At each end of chamber 10, sleeve 24 is stabbed over interior projection 15 and bottomed out in the trepanned groove 14 of an end piece 11.

The growth compartment 5 is located between the interior bore of the sleeve 24, the membrane carrier assembly 27, and the interior ends of the interior projection 15 of the end pieces 11. The growth compartment 5 is transversed by a membrane carrier assembly 27 as shown in FIGS. 1 and 3. An end of the generally cylindrical membrane carrier assembly 27 is mounted in the counterbore 19 of each of the two end assemblies 11 used in chamber 10.

Figure 4:
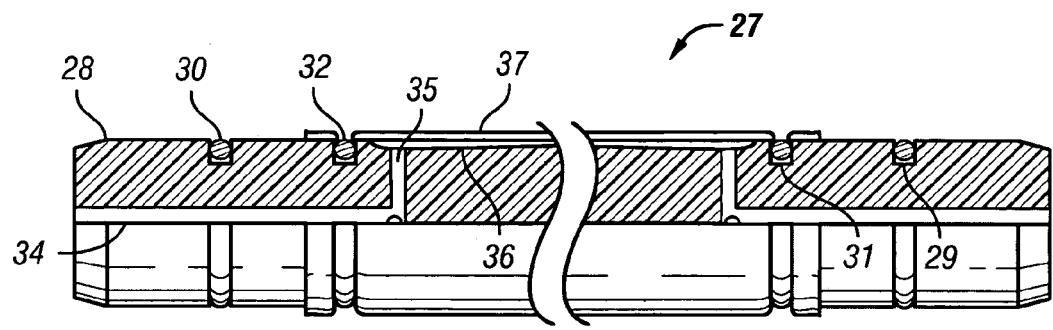
FIG. 4 shows a longitudinal quarter-sectional view of the membrane carrier assembly used in FIG. 1.

FIG. 4 shows the details of construction of membrane carrier assembly 27. Support cylinder 28 is symmetrical about its transverse midplane. The exterior of each end of cylinder 28 has, sequentially from its end, a lead-in taper to ease blind stabbing into a mounting hole, a first annular male O-ring groove 29 mounting elastomeric O-ring 30, and a second groove 31 configured similarly to an O-ring groove. Each end of cylinder 28 also has an axial blind hole 34 with multiple (in this case, four) equispaced coplanar radial cross holes 35 intersecting the inner end of blind hole 34. A small recessed surface pocket 36, having an arcuate cross-section, is located on the exterior of cylinder 28 and is intercepted by each radial cross hole 35. The depth of surface pockets 36 below the outside cylindrical diameter is largest near the intersection with its cross hole 35 and linearly tapers to zero towards the middle of cylinder 28. Thus, the cylinder 28 has a fluid channel at each end (i.e., the blind hole 34, radial cross holes 35 and the surface pockets 36) that provide fluid communication between the ends of the cylinder to the exterior surface of the middle section of the cylinder.

Centrally deployed with a close fit around the exterior of cylinder 28 is a tubular molecular weight cut-off membrane 37. Membrane 37 is flexible with a limited amount of elastic stretch capability. The construction of membrane 37 is very carefully controlled so that the number of molecules, having a molecular weight in excess of the specific limiting molecular weight cut-off value of the membrane 37, transfused through the membrane in either direction is statistically very small and rapidly decreases as a function of increasing molecular weight. Thus, there is essentially no passage of molecules, much larger than the molecular weight cut-off value of the membrane, through the membrane 37. The molecular weight cut-off value of the membrane 37 is preselected so that nutrients and growth factors, as well as metabolic waste products, can easily transfuse through the membrane, whereas larger cellular products can be retained. For example, Factor VIII (having a molecular weight of about 350,000 daltons) or IgG monoclonal antibodies (having a molecular weight of about 155,000 daltons) produced by genetically engineered bacteria or cells can be retained by a membrane with a molecular weight cut-off value of about 100,000 daltons; whereas the majority of serum albumin (having a molecular weight of about 67,500 daltons and making up 55% to 62% of serum protein) would be allowed to pass through the membrane.

Currently bioreactors and culture chambers are designed to have a filter to keep the cells within the chamber and to allow the desired therapeutic protein to pass out of the chamber with the waste products. The present invention also allows the user to select a membrane having a molecular weight cut-off value that would allow the desired protein to pass out of the culture chamber with the waste products. However, the present invention also permits the user to select a membrane having a smaller molecular weight cut-off value than the desired protein, so that the desired protein is retained within the culture chamber and is concentrated with time as the cells multiply and continue to produce the desired protein. Since the culture chamber 10 is reusable, the membrane carrier assembly 27 can be assembled with membranes 37 having a variety of molecular weight cut-off values depending on the protein being produced.

Furthermore, the membrane carrier assembly 27 of the present invention provides a media circulating system that allows the user to constantly monitor certain media parameters in the culture chamber (e.g., the pH) and to adjust those parameters by adjusting the media being pumped into the culture chamber, thereby maintaining optimum conditions for the cells being cultured.

Figure 5:
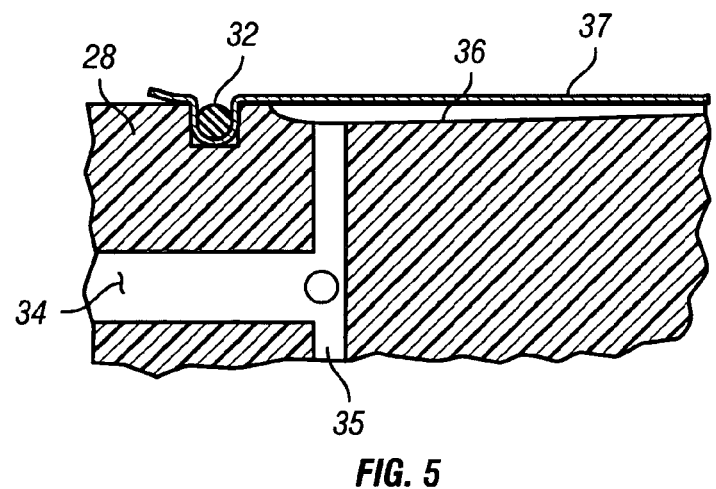
FIG. 5 is a partial longitudinal cross-section of the membrane assembled on one end of the membrane carrier assembly of FIG. 4.

As shown in FIG. 5, membrane 37 is sealed to the exterior of cylinder 28 by using O-ring 32 to circumferentially constrict over the exterior of membrane 37, thereby forcing it into sealing engagement with groove 31 on the outside of cylinder 28. In this manner, a small chamber in fluid connection with the radial flow passage 35 is formed between the exterior of surface pockets 36 and the interior of membrane 37. The depth and length of cut for the surface pockets 36 is predetermined to be sufficient to produce a sufficient pressure area so that the elastic resistance of membrane 37 can be overcome. The expansion of the membrane 37 when media is passed through flow passage 35 and along pockets 36 permits a thin flow sheet of media between the membrane 37 and cylinder 28 to be established.

Figure 6:
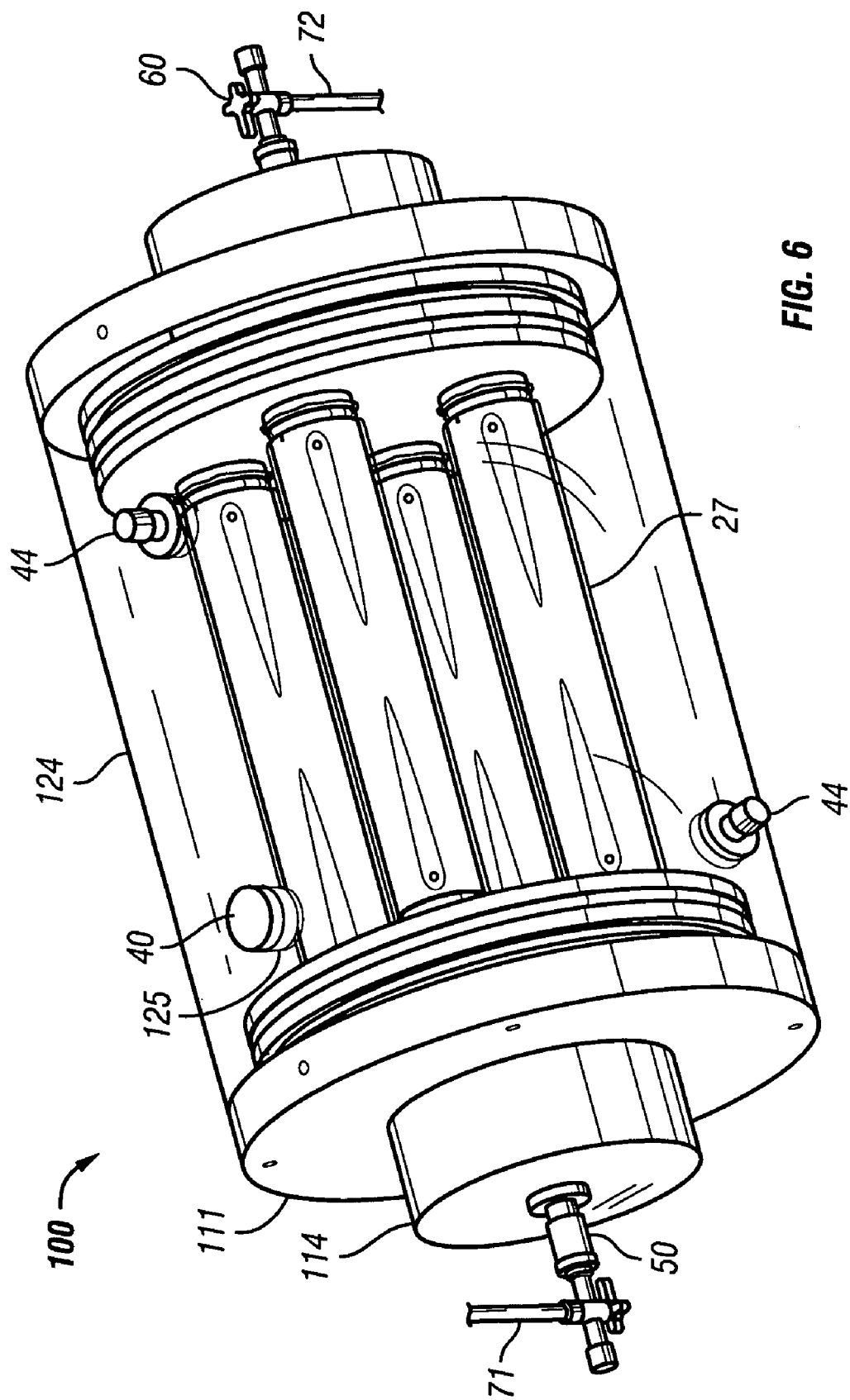
FIG. 6 shows another embodiment of the cell culture chamber of the present invention using an internal array of multiple membranes supported by membrane carrier assemblies.
Figure 7:
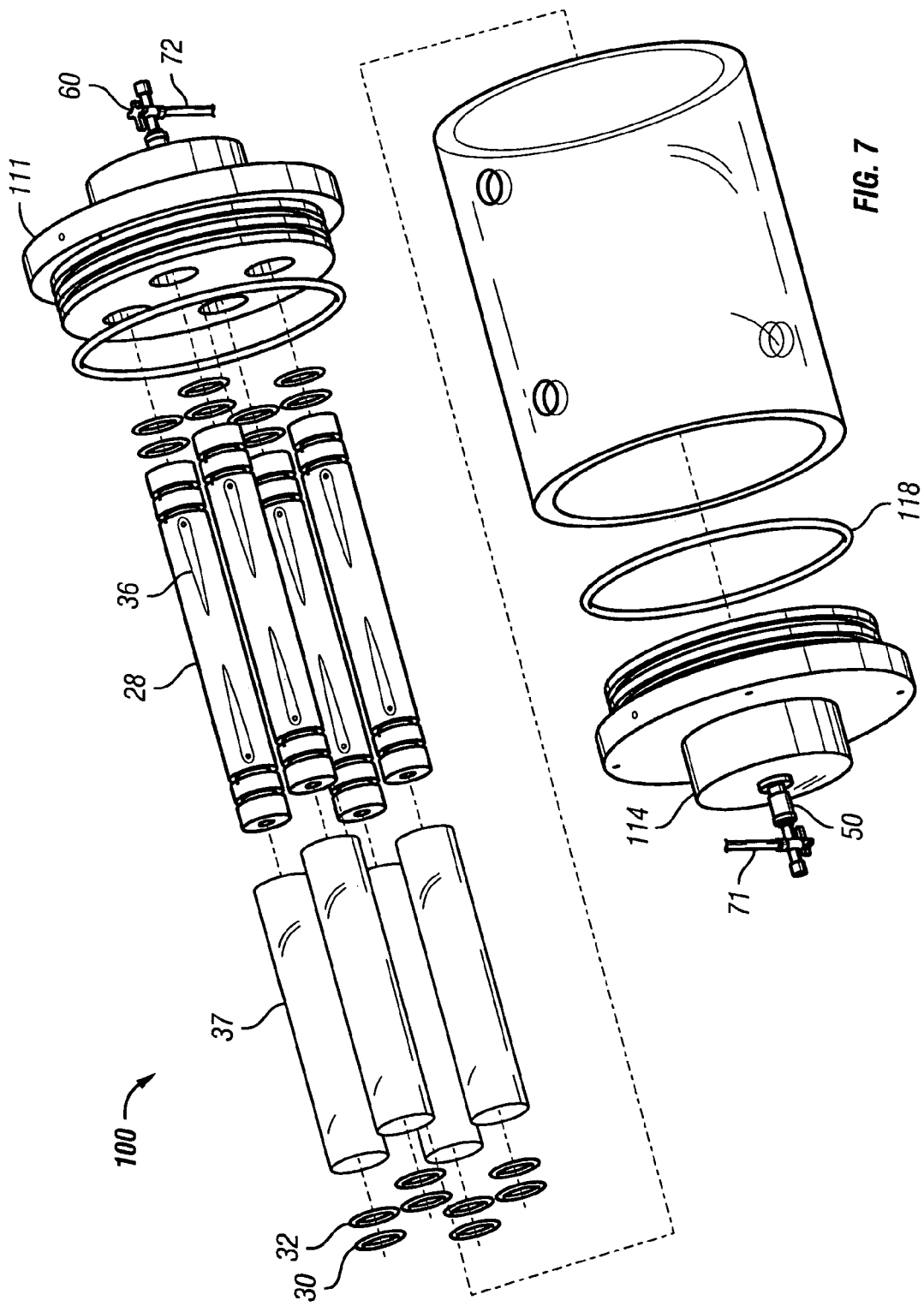
FIG. 7 is a partially exploded oblique view of the assembly shown in FIG. 6.
Figure 8:
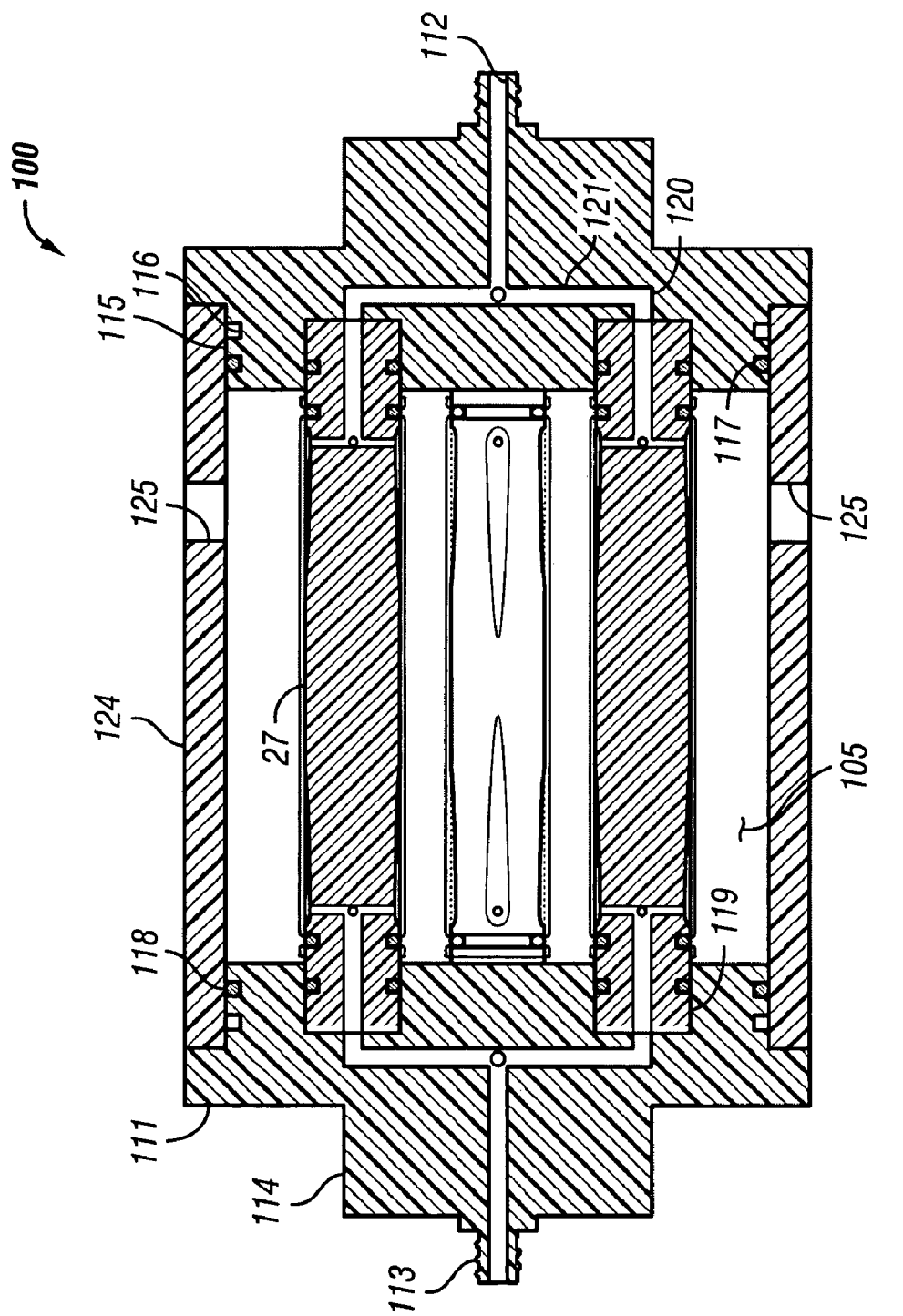
FIG. 8 is a longitudinal cross-sectional view of the apparatus of FIG. 6 with the end swivels and shutoff valves removed.

FIGS. 6-8 show a second embodiment of a reusable culture chamber. The culture chamber 100 is similar in many ways to the first described culture chamber 10. Both culture chambers 10 and 100 use common components. In general, the culture chamber 100 is used for larger volume preparations than the culture chamber 10, given that the growth media was the same. If, on the other hand, the nutrients and/or waste products were slow to diffuse through the growth compartment 5 of culture chamber 10 due to use of a more restrictive molecular weight cut-off membrane, the multi-membrane carrier arrangement of culture chamber 100 might be used in a relatively small culture chamber.

As can be seen in FIGS. 6-8, two identical end pieces 111 seal to the ends of right circular cylindrical tubular sleeve 124 so that a growth compartment 105 is formed within the enclosed space. When in use for culturing cells and other biologicals, the culture chamber 100 is designed to be supported on and rotated by a roller drive that rotates the chamber about its axis. Thus, the culture chamber 100 is typically round in construction. Fluid-conducting swivels 50, stopcock valves 60, and fluid inlet tubing 72 and outlet tubing 71 are provided on the ends of the housing 100 so that the nutrient fluid and its attendant waste fluid may be delivered and controlled. Multiple radial wall penetration ports 125 are provided in the annular wall of sleeve 124 to allow the introduction of one or more fill ports 40 and one or more vent ports 44.

The construction details of the culture chamber 100 are best understood by reference to FIGS. 7 and 8. End piece 111 has a right circular cylindrical central flange body of the same outer diameter as that of sleeve 124. End piece 111 has a coaxial outwardly extending reduced diameter cylindrical neck 114 with a coaxial push-on hose barb attachment neck 113 on its outer transverse face. Axial through hole 112 penetrates through the attachment neck 113 and intersects four equispaced coplanar radial holes 121 which extend outwardly to approximately half the maximum outer diameter of the central body of end piece 111.

Reduced diameter coaxial right circular cylindrical interior projection 115 extends inwardly on the transverse face of the interior end of the central section of end piece 111. The exterior cylindrical surface of interior projection 115 has, in order from the interior transverse face of end piece 111, first and second annular male O-ring grooves 117 and 116. Elastomeric O-ring 118 is mounted in O-ring groove 117. At the interior end of interior projection 115 of end piece 111, an array of flat-bottomed counterbores 119 (in this case four) are all located at the same radius and have coaxial blind holes 120 at their inner ends. Each blind hole 120 intersects the outer end of a corresponding radial hole 121. Although not shown, an optional lead-in chamfer may be provided at the mouth of counterbore 119 in order to facilitate the stabbing of an O-ring seal.

Right circular cylindrical sleeve 124, preferably made of acrylic plastic as previously described for sleeve 24, may be provided with lead-in tapers on its interior corners to facilitate the stabbing of O-rings. The interior bore of sleeve 124 is a close sliding fit to the outer diameter of interior projection 115 of end fitting 111, thereby permitting O-ring 118 to sealingly engage the bore of sleeve 124. As stated previously, the sleeve 124 has multiple radial wall penetration ports 125 to allow the mounting of fill ports 40 and vent ports 44 (not shown, but similar to those in the culture chamber 10). The fill ports 40 are used for inserting fluids into or removing fluids from the interior of the growth compartment 105 while the chamber 100 is in service but not rotating. Vent ports 44 are used to allow gas to escape from the growth compartment 105 as it is being filled with media. Each end of sleeve 124 is stabbed over interior projection 115, sealed against an O-ring 118, and shouldered against the interior transverse face of the central portion of an end piece 111, so that a sealed growth compartment 105 is formed between end pieces 111, the interior of tube 124, and around the membrane carrier assemblies 27.

The corresponding counterbores 119 in both end pieces 111 are coaxially aligned so that a cylindrical membrane carrier assembly 27 is stabbed and bottomed in the corresponding counterbores of each of the two end pieces 111. The membrane carrier assemblies 27 are identical to that used in the culture chamber 10 and shown in FIG. 4.

Figure 9:
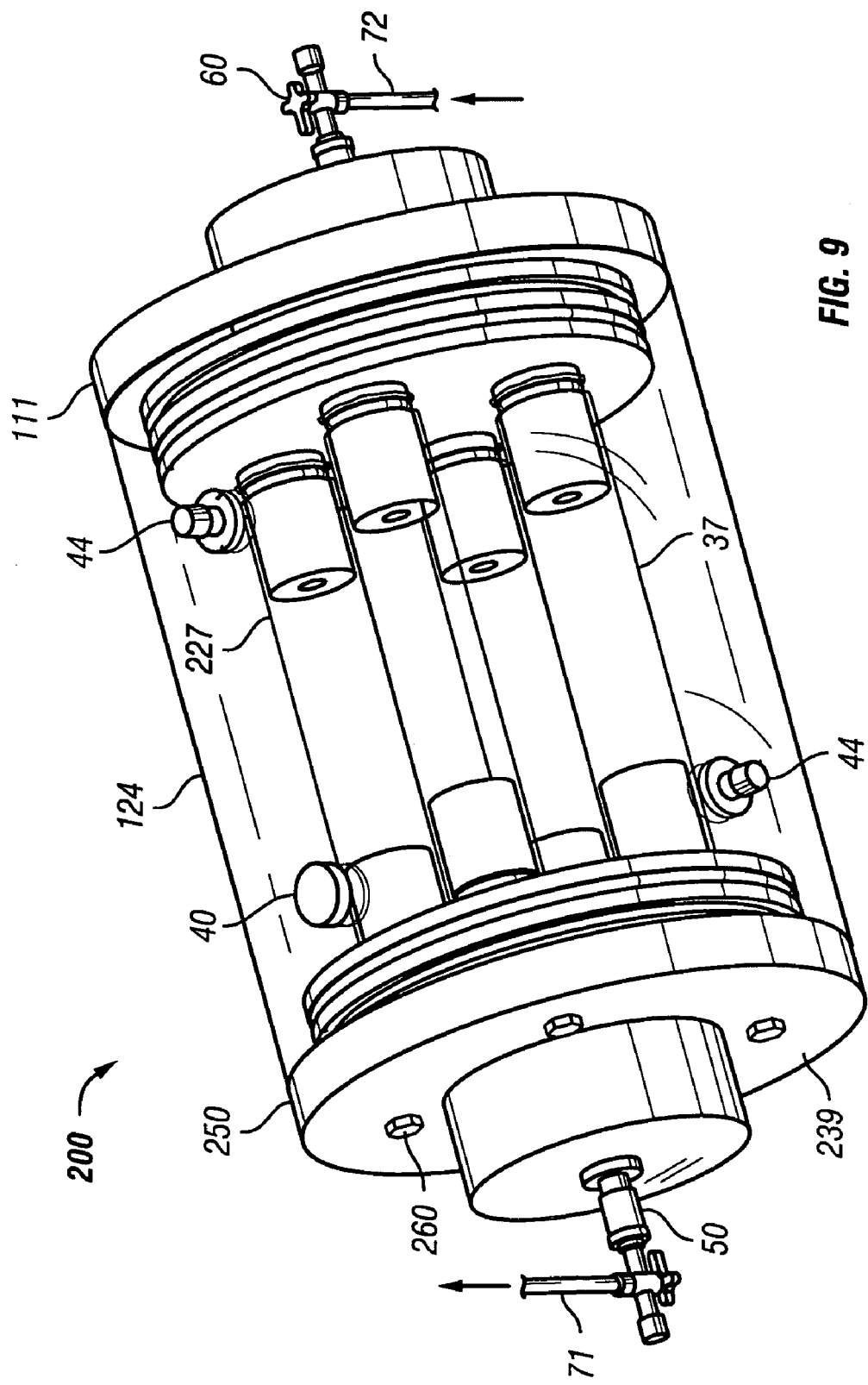
FIG. 9 shows an oblique view of another embodiment of the culture chamber.
Figure 10:
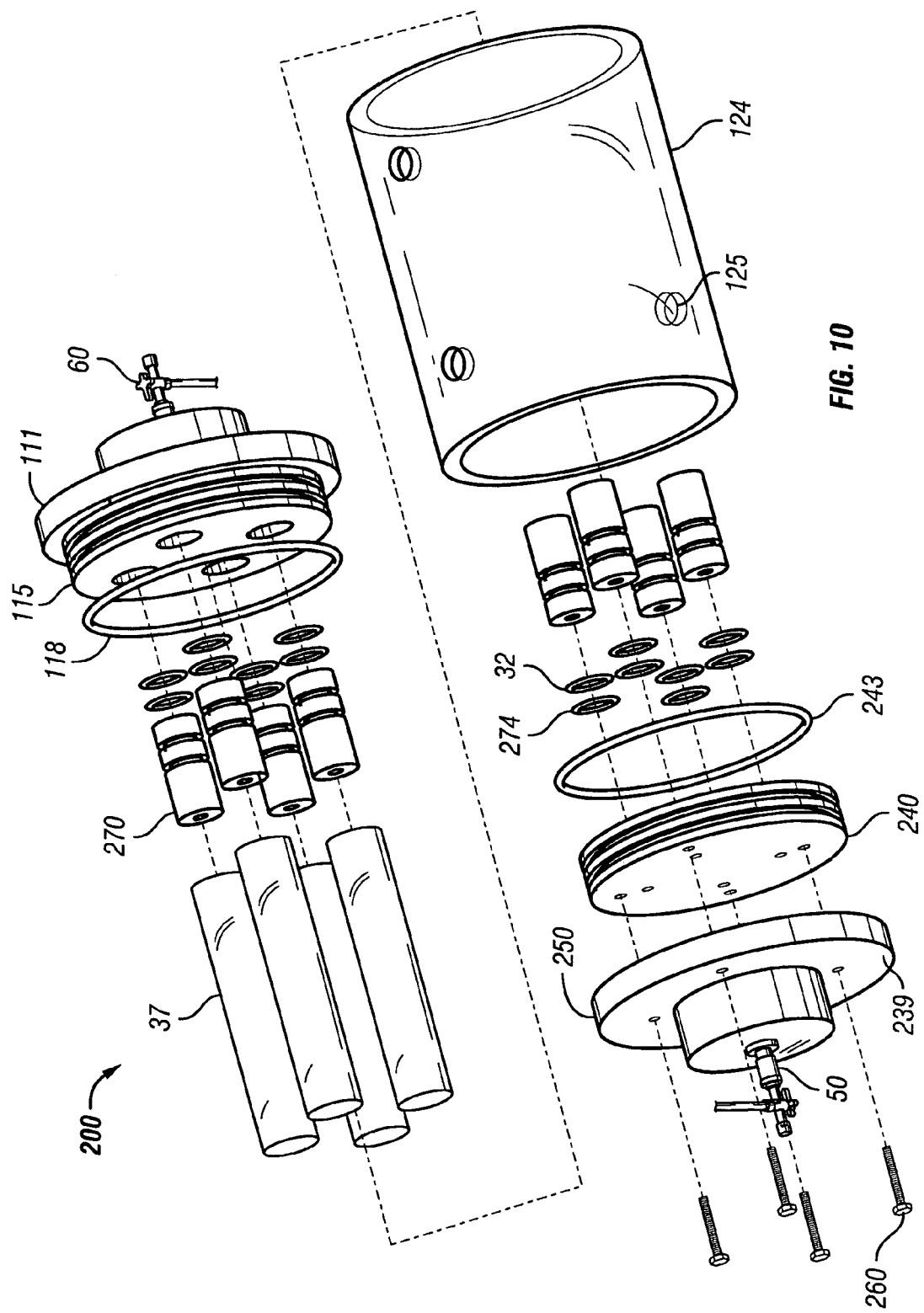
FIG. 10 is an exploded oblique view of the embodiment shown in FIG. 9.
Figure 11:
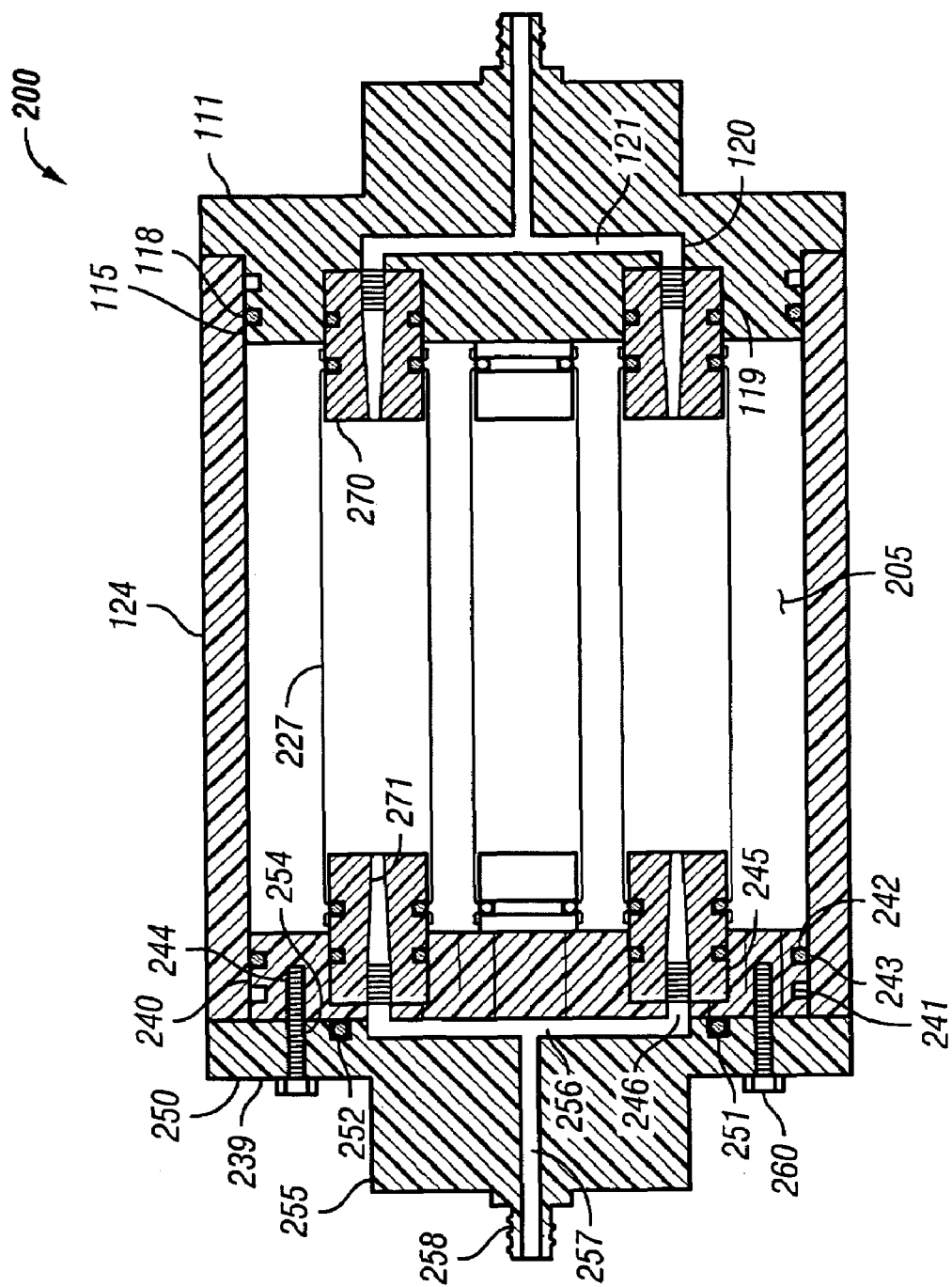
FIG. 11 is a longitudinal cross-sectional view of the apparatus of FIG. 9 with the end swivels and shutoff valves removed.

A third embodiment, culture chamber 200, of a reusable culture chamber of the present invention is shown in FIGS. 9-11. Culture chamber 200 also uses multiple molecular weight cut-off membranes 37 mounted within the interior of the growth compartment 205. However, the structural mounting of the membranes for this embodiment is different than that used for the previously described embodiments. Although the culture chamber 200 and culture chamber 100 include different components, these two culture chambers are structurally similar and use several common components, including the sleeve 124, the end piece 111, the swivels 50, the stop cocks 60, and the tubings 72 and 71.

The culture chamber 200 is typically round in construction as it is designed to be supported on and rotated by a roller drive that rotates the chamber about its axis. Fluid-conducting swivels 50, stopcock valves 60, and fluid inlet tubing 72 and outlet tubing 71 are provided on the ends of the housing 200 so that the nutrient fluid is added to and mixed with the media in the growth compartment 205 and waste products are removed from the growth compartment 205 through the membrane and out the culture chamber 200. Multiple radial wall penetration ports 125 are provided in the annular wall of sleeve 124 to allow the introduction of one or more fill ports 40 and one or more vent ports 44.

As seen in FIGS. 10 and 11, two outwardly similar end pieces 111 and 239 seal to the ends of right circular cylindrical tubular sleeve 124 so that a growth compartment 205 is formed within the enclosed space. The inlet end piece 111 is identical to that used for the culture chamber 100. The outlet end piece 239 is basically a two-piece version of the inlet end piece 111.

Outlet end piece 239 is conformed similarly to the inlet end piece 111, but is built in two main pieces, inner plug 240 and outer flange 250, in order to permit assembly. Inner plug 240 is a right cylindrical disk having the same inner diameter as the sleeve 124 with which it is mated. Inner plug 240 has a first O-ring groove 241 and a second O-ring groove 242 on its outer circumference. O-ring 243, which seals between sleeve 124 and inner plug 240, is positioned in the male O-ring groove 242.

On its inner transverse face, plug 240 has a number of equispaced flat-bottomed counterbored socket holes 245. For example, FIGS. 9 and 10 show four socket holes 245. Although not shown, the socket holes 245 may have chamfered lead-ins to facilitate O-ring passage. Each socket hole 245 has a short small diameter coaxial through hole 246 penetrating from its socket 245 to the outer transverse face of inner plug 240. On the outer transverse face of plug 240, four equispaced drilled and tapped blind holes 244 are located on a concentric bolt circle. The exterior face of plug 240 is flush with the end of sleeve 124.

Outer flange 250 is a right circular cylindrical disk with its outer diameter equal to that of sleeve 124 and having a concentric reduced diameter right circular cylindrical extension 255 on its outer transverse face. Coaxial push-on hose barb attachment neck 258 is positioned on the outer transverse face of extension 255 and axial through hole 257 penetrates through both the attachment neck 258 and the rest of the body of outer flange 250. The inner transverse face of outer flange 250 abuts the transverse end of sleeve 124 and has concentric O-ring face groove 251 mounting O-ring 252 located there. O-ring 252 seals between inner plug 240 and outer flange 250 to prevent leakage in the radial direction.

Shallow flat-bottomed counterbore 256 is located on the interior transverse face of flange 250 inside of O-ring groove 251 and is intersected by through hole 257. The diameter of counterbore 256 is such that it extends to the outer periphery of the through holes 246 in inner plug 240 so that fluid communication is possible. Four through clearance holes 254 penetrate outer flange 250 on the same bolt circle pattern as for drilled and tapped holes 244 on the inner plug 240. Machine screws 260 pass through holes 254 and are threadedly engaged into tapped holes 244 in order to clamp inner plug 240 and outer flange 250 together to form outlet end piece 239.

Figure 12:
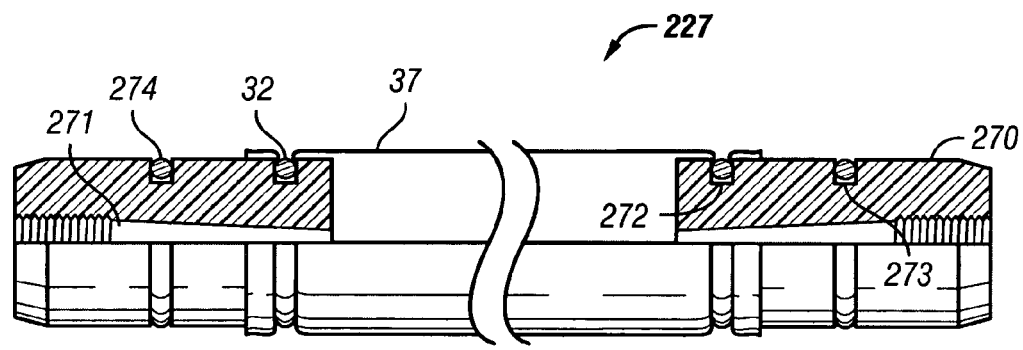
FIG. 12 shows a longitudinal quarter-sectional view of the membrane carrier assembly used in FIG. 9.

Referring to FIG. 12, the diffuser assembly 227 used in the culture chamber 200 is shown in a longitudinal quarter-section. The arrangement of diffuser assembly 227 differs from that of the previously described membrane carrier assembly 27. In particular, rather than using a one-piece cylindrical core for the mounting of the membrane 37, the diffuser assembly 227 uses two separate end plugs 270 which mount the molecular cutoff membrane suspended between them. The resulting assembly has the same length overall as the equivalent carrier membrane assembly 27, so that the membrane carrier assembly 27 can be used in place of diffuser assembly 227. However, diffuser assembly 227 cannot be used with either culture chamber 10 or 100, since it lacks the axial compressive stiffness required for assembly into those chambers.

End plug 270 is a right circular cylinder with concentric through bore 271 extending through its length. The outer end of bore 271 is drilled and tapped for assembly purposes so that it may be blindly aligned and pulled into engagement with its comating mounting counterbored socket 245 in inner plug 240. The exterior of end plug 270 has, from its outer end, a lead-in taper to facilitate stabbing into a mounting receptacle such as socket 245 or 119 in end piece 111, male O-ring groove 273, and rectangular profile retention groove 272. O-ring 274 is mounted in groove 273.

The tubular molecular weight cut-off membrane 37 used in culture chamber 200 is identical in its shape and size to that used in the other configurations of the culture chamber. Membrane 37 is stretched over the interior end of end plug 270 past groove 273 and then sealingly retained on plug 270 by using O-ring 32 to force the membrane tightly into groove 272. One end plug 270 with its O-rings 274 and 32 is used on each end of the membrane 37 to complete the assembly of the diffuser assembly 227.

To construct cell culture chamber 200, each assembled diffuser assembly 227 has one end inserted sealingly into its corresponding socket 119 in end piece 111 until it bottoms out. The sleeve 124 is then assembled over the cylindrical inner end 115 of end piece 111 with O-ring 118 in place to effect a seal. At this point, inner plug 240 is aligned with end piece 111, assembled with its O-ring 243, and machine screws or studs (not shown) are extended inwardly through holes 246 and engaged in the tapped portion of bores 271 of the free end of diffuser assembly 227. After inner plug 240 is installed with its outer transverse face approximately flush with the end of sleeve 124, the screws or studs inserted into bores 271 of the diffuser assembly 227 can be used to pull the individual engaged end plugs 270 fully into the sockets 245 of inner plug 240 where they are in sealing engagement. At that point, the assembly screws or studs can be removed from plug 240 and end plugs 270 so that the end flange 250 can be attached to plug 240 using screws 260 and the assembly completed.

Culture Chambers with Disposable Bioreactor Bags

The present invention also includes culture chambers having a reusable bag housing to provide support for a disposable bioreactor bag. Since the bag assemblies are designed to be supported by a bag support housing, very large capacity bag assemblies can be used to scale-up production procedures. The bag assemblies described herein are made to hold anywhere from milliliters to thousands of liters of fluid. Furthermore, the bag assemblies described herein are pre-sterilized before use. Sterilization is typically done using gamma radiation or gas.

The bioreactor bags are housed in a rotatable housing and rotated by a drive mechanism as described in copending U.S. patent application Ser. No. 10/283,000 entitled "Disposable Culture Bag" and filed on Oct. 29, 2002. U.S. patent application Ser. No. 10/283,000 is incorporated herein by reference. The disposable bioreactor bags have rigid end pieces that can be configure to carry one or more membrane carrier assemblies 27 or one or more diffuser assemblies 227 with molecular weight cut-off membranes 37.

Figure 13:
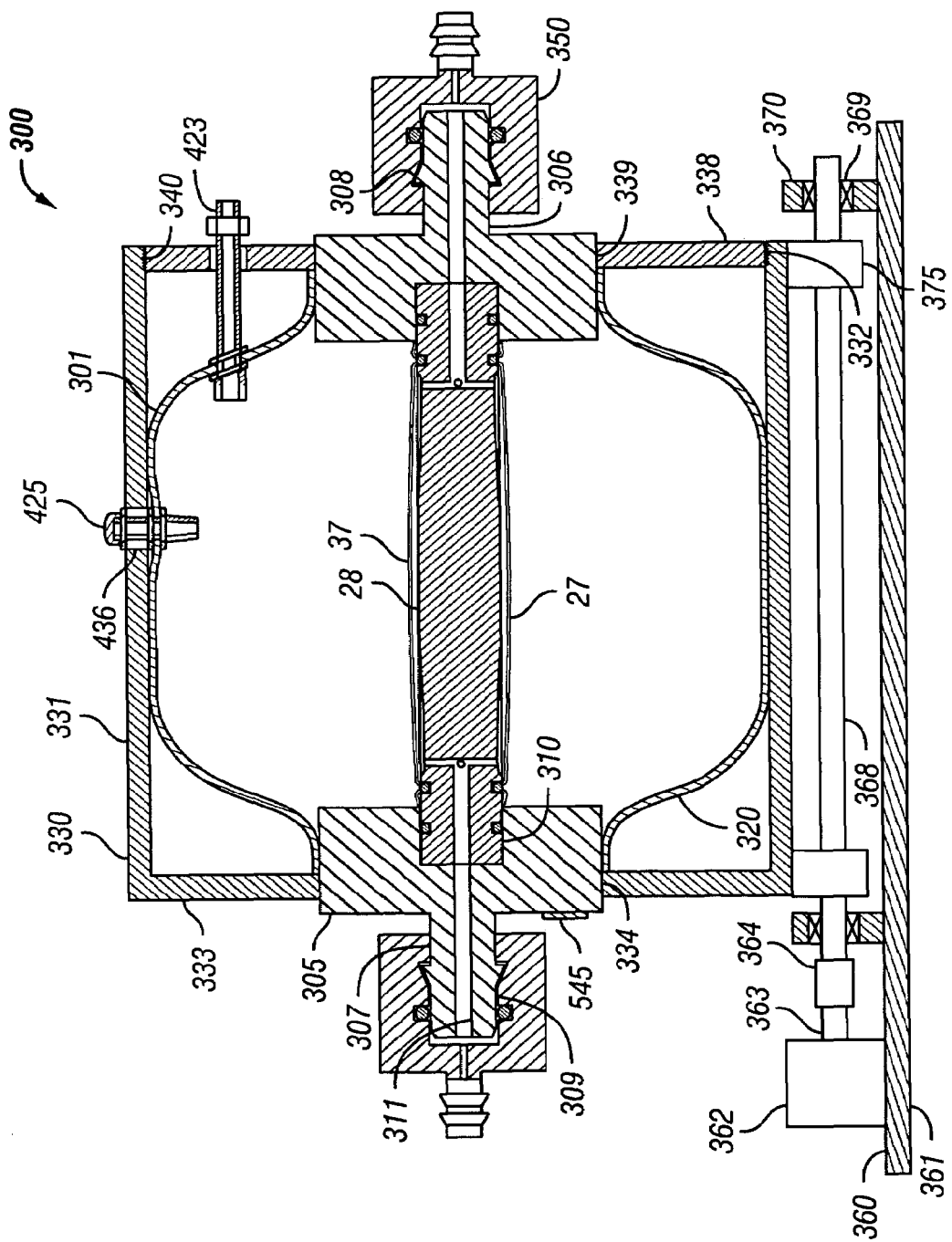
FIG. 13 is a longitudinal sectional view of another embodiment of the cell culture chamber of the present invention mounted on a drive that is used to provide a slow rotation to the culture chamber.

FIG. 13 shows a first embodiment of a culture chamber 300 of the present invention having a disposable bioreactor bag assembly 301. As shown in FIG. 13, bag assembly 301 includes bag 320, two end pieces 305 for establishing fluid interconnections and positioning the bag assembly 301, and a centrally positioned membrane carrier assembly 27. Bag assembly 301 also includes one or more gas vent removal ports 425 and one or more fill ports 423.

All of the components of bag assembly 301 which contact the biological media and which are supplied to and removed from the bag assembly are biologically non-reactive, non-toxic and exhibit low protein binding properties. Bag assembly 301 and its constituent components are fused together with heat and pressure. However, the term fusing will be used with reference to joining elements of the bag assemblies of this invention where the elements are joined using heat, adhesive, ultrasonic welding, or other suitable means to effect the connections.

Preferably the bag 320 is made of a plurality of layers such as the multilayered fabric construction used in the synthesis of custom bags manufactured by Newport Biosystems, Inc. (Anderson, Calif.). For example, a typical four-ply fabric construction would have individual layers, sequentially from the outer bag layer, of nylon, polyvinyldichloride (PVDC), a linear low density polyethylene (LLDPE), and a LLDPE inner layer for contacting the cells and the biological media. The plies of the bag have thicknesses with physical and molecular properties to provide the desired puncture strength, tensile strength, flexural strength, cell and gas and liquid permeabilities in appropriate ranges, and weldability and/or bondability or fusibility. The desired permeabilities typically are low or zero. However, variations of the bag 320 are designed to be gas-permeable for certain applications.

Bag end 305 is a right circular cylindrical disk having a concentric connecting neck 306 on its outer transverse face. Connecting neck 306 has, in sequential order from the outer face of bag end 305, a straight cylindrical shank 307, an externally projecting frustro-conical latching shoulder 308, and a second straight cylindrical outer shank 309. The inward end of the frustro-conical latching shoulder 308 is a transverse shoulder, while the outward end has the same diameter as that of second shank 309. The interior end of bag end 305 has a concentric flat-bottomed counterbore 310 which is intercepted by axial through hole 311 which penetrates through the remainder of bag end 305 and connecting neck 306. The diameter of counterbore 310 is such that it provides a close fit to the outer diameter of support cylinder 28 of the membrane carrier assembly 27. Bag end 305 is circumferentially welded or otherwise fused on its outer diameter to the end of bag 320.

The membrane carrier assembly 27 is substantially identical to that used in culture chambers 10 and 100 and shown in detail in FIG. 4. The carrier assembly 27 has its ends slipped into and bottomed in the comating counterbores 310 on the interior faces of the bag ends 305. The O-ring 30 provides a seal between the counterbore 310 and the membrane support cylinder 28 of the carrier assembly 27. FIG. 4 shows the molecular weight cut-off membrane 37 retained in place over the outer diameter of the central portion of support cylinder 28 by O-ring 32. O-ring 32 seals and anchors the end of membrane 37 into the groove 31. Alternatively, the molecular weight cut-off membrane 37 may also be bonded or fused to the ends of the support cylinder 28.

The disposable bioreactor bag assemblies have flexible walls and are supported by a bag support housing. Numerous configurations of a bag support housing can be used. One example of a bag support housing 330, shown in FIG. 13 consists of a bag support end 331 and bag support closure 338. The bag support assembly 300 may be constructed of a variety of materials known in the art, but will preferably be constructed of either a metal, such as stainless steel, or a solid plastic, such as Plexiglas™ or acrylic. Although the bag support housing may be made any shape, the housing is preferably cylindrical to ease its horizontal rotation.

The bag support end 331 has a thin-walled right circular cylindrical section and a transverse bulkhead 333 at a first end of the cylindrical section. The inner diameter of the bag support end 331 is sized to provide a close slip fit to the filled bioreactor bag assembly 301. The transverse bulkhead has a concentric circular hole 334 sized to closely fit with the exterior cylindrical surface of bag end 305 and a thickness of approximately 0.5 to 0.1 inch. The bag support end 331 has female threads 332 at its second, opposed end. Multiple radial wall penetration ports 436 are provided in the annular wall of the bag support end 331 to allow the introduction of one or more vent ports 425 and one or more fill ports 423 in the bag assembly 301.

Bag support closure 338 is a round disk with a central circular hole 339 that closely fits the outer diameter of bag end 305 and outer holes designed to fit vent ports 425 or fill ports 423 in the bas assembly 301. The bag support closure 338 has a thickness of approximately 0.5 to 0.1 inch. The exterior cylindrical surface of bag support closure has male threads 340 comatable with the female threads 332 of bag support end 331 so that the two items may be screwed together to create a housing 330 having coaxial end holes 334 and 339.

Drive assembly 360 may have a variety of designs. In this embodiment the drive assembly 360 is similar to that used in U.S. Pat. No. 6,080,581, which is hereby incorporated by reference, where a rigid cylinder was used as the rotating bioreactor. Two parallel, spaced-apart, journaled shaft assemblies support the bag support housing 330 that contains bag assembly 301. Each of the two journaled shaft assemblies has a set of one or more equidiameter rollers 375 mounted on it and the bag support housing 330 is tangential to both sets of rollers. At least one and, possibly, both shaft assemblies are driven. A drive assembly 360 consists of variable speed motor 362 which has its output shaft 363 connected to main shaft 368 by cylindrical shaft coupling 364. Main shaft 368 is journaled in two places near its ends by bearings 369, which are in turn supported by pillow blocks 370. Equidiameter rollers 375 are concentrically mounted on main shaft 368 adjacent the pillow blocks 370 and positioned to support the bag support housing 330 close to its ends.

Motor 362 is mounted on base plate 361, as are the pillow blocks 370. If an undriven idler shaft assembly is used, then the shaft coupling 364 and motor 362 are omitted. If both shaft assemblies are driven, then they must be synchronized to run at the same speed. The motor driver or drivers are not indicated in FIG. 13, and axial keeper rollers for maintaining bag support assembly 330 centered on the rollers of the shaft assemblies likewise are not shown. Both of these items and other minor items are well understood by those skilled in the art and are not essential for understanding the present invention.

Figure 14:
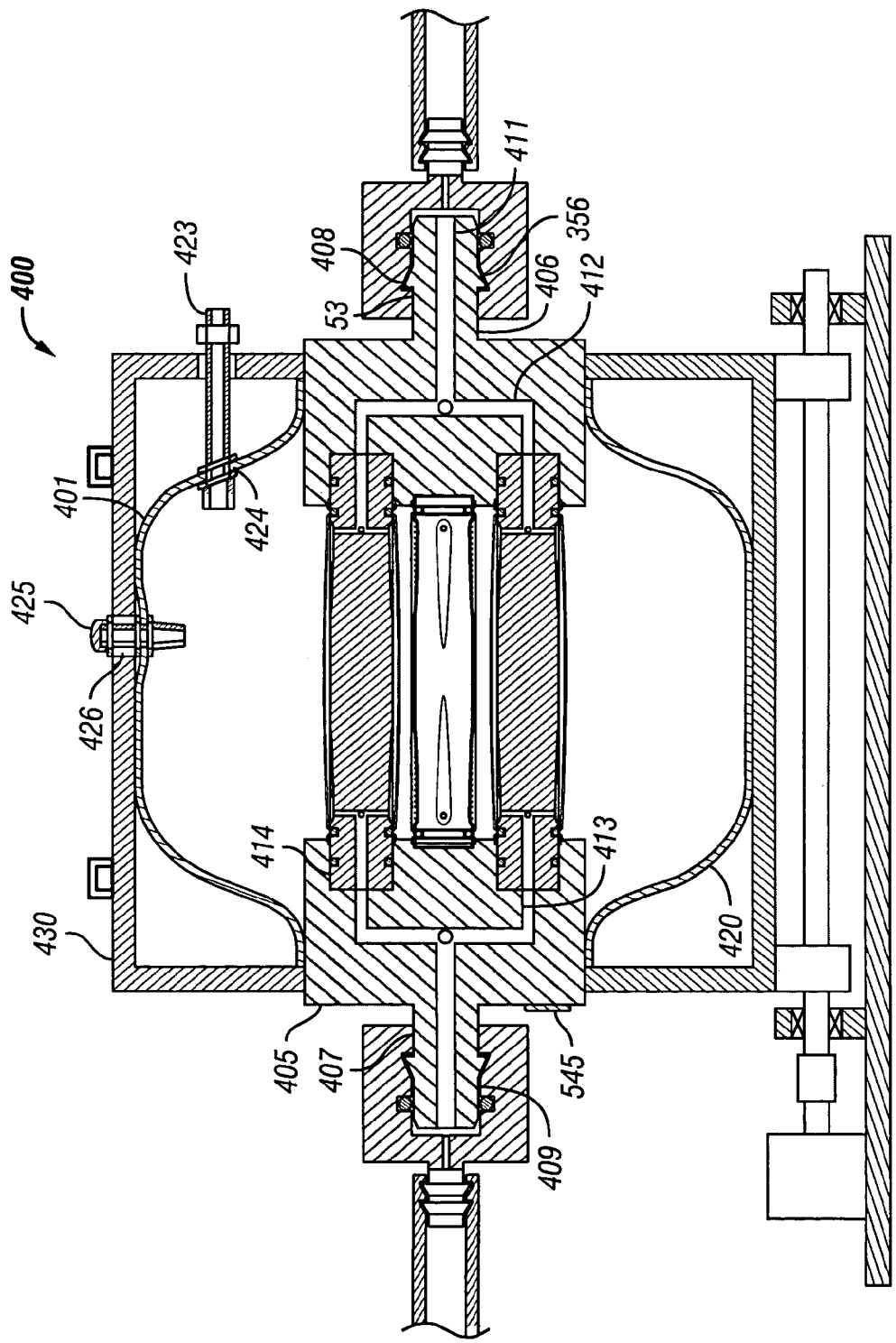
FIG. 14 shows a longitudinal cross-sectional view of another embodiment of the present invention.

FIG. 14 shows another embodiment of the culture chamber 400 adapted for use with a disposable bioreactor bag 401. The bag assembly 401 includes bag 420, two end pieces 405 for establishing fluid interconnections and positioning the bag assembly 401. A major difference between the culture chamber 300 and 400 is that the bag assembly 401 of the culture chamber 400 is configured to mount multiple membrane carrier assemblies 27 in an array symmetrical about the longitudinal axis of bag 420.

Bag assembly 401, like the bag assembly 301, includes multiple service ports such as a gas venting port 425 and a fill port 423. The fill port 423 is bonded into a penetration 424 in the side of bag 420. The vent port 425 is bonded into a penetration 426 in the side of bag 420. The attachments of ports 423 and 425 into bag 420 are reinforced by sealing grommets on both sides of the bag wall, as is well understood by those skilled in the art.

As described for the bag assembly 301, the bag assembly 401 has its constituent components welded or bonded or fused together. Furthermore, all of the components of the bag assembly 401 contacting the biological media are biologically non-reactive, non-toxic and exhibit low protein binding properties.

Preferably the bag 420 is made of a plurality of layers such as the multilayered fabric construction used in the synthesis of custom bags manufactured by Newport Biosystems, Inc. (Anderson, Calif.), as previously described for the bag 320 in the fourth cell growth chamber embodiment 300.

Bag end 405 is a right circular cylindrical disk having a concentric connecting neck 406 on its outer transverse face. Connecting neck 406 has, in sequential order from the outer face of bag end 405, a straight cylindrical shank 407, an externally projecting frustro-conical latching shoulder 408, and a second straight cylindrical outer shank 409. The inward end of the frustro-conical latching shoulder 408 is a transverse shoulder, while the outward end has the same diameter as that of second shank 409. Coaxial hole 411 is located on the axis of connecting neck 406 and penetrates through the length of connecting neck 406 and part way into the main cylindrical body of bag end 405.

Hole 411 is intersected by four equispaced radial cross holes 412 which extend from the central axis of bag end 405 approximately halfway to the outer cylindrical face. The interior end of bag end 405 has four equispaced flat-bottomed counterbores 414. Each counterbore 414 is intercepted by a short coaxial blind hole 413, which is in turn intercepted by a cross hole 412. Accordingly, a fluid path is created from the hole 411 transversing connecting neck 406, through the cross holes 412 and the short connecting holes 413 into each of the counterbores 414.

The diameter of counterbore 414 is such that it provides a close fit to the outer diameter of support cylinder 28 of the membrane carrier assembly 27. A bag end 405 is circumferentially welded or otherwise fused on its outer cylindrical face to the corresponding end of bag 420 at its end opening. The bag ends 405 are aligned so that their counterbores 414 are coaxial prior to attachment to the bag 420.

The membrane carrier assembly 27 transversing the bag assembly 401 has been previously described and is shown in detail in FIG. 4. Each of the carrier assemblies 27 has its ends slipped into and bottomed in the comating counterbores 414 on the interior faces of the bag ends 405. The O-rings 30 provide a seal between the counterbore 414 and the support cylinder 28 of the carrier assembly 27. The membrane 37 is retained in place over the outer diameter of the central portion of support cylinder 28 by the use of O-rings 32 to seal and anchor each end of membrane 37 into each groove 31.

Bag assembly 401 has identical inlet and outlet fluid coupling swivel joints 350 to allow the. bag assembly 401 to freely rotate with its bag support housing 430 while connected to the input and output fluid feed tubings 72 and 71. The swivel 350 is latched onto neck 406 so that relative axial motion is prevented by having the shoulder of frustro-conical latching shoulder 408 abut the corresponding shoulder of the recess 356 of counterbore 353 in the swivel 350. The connection is a one-way snap connection effected when neck 406 is forced into counterbore 353.

Figure 18:
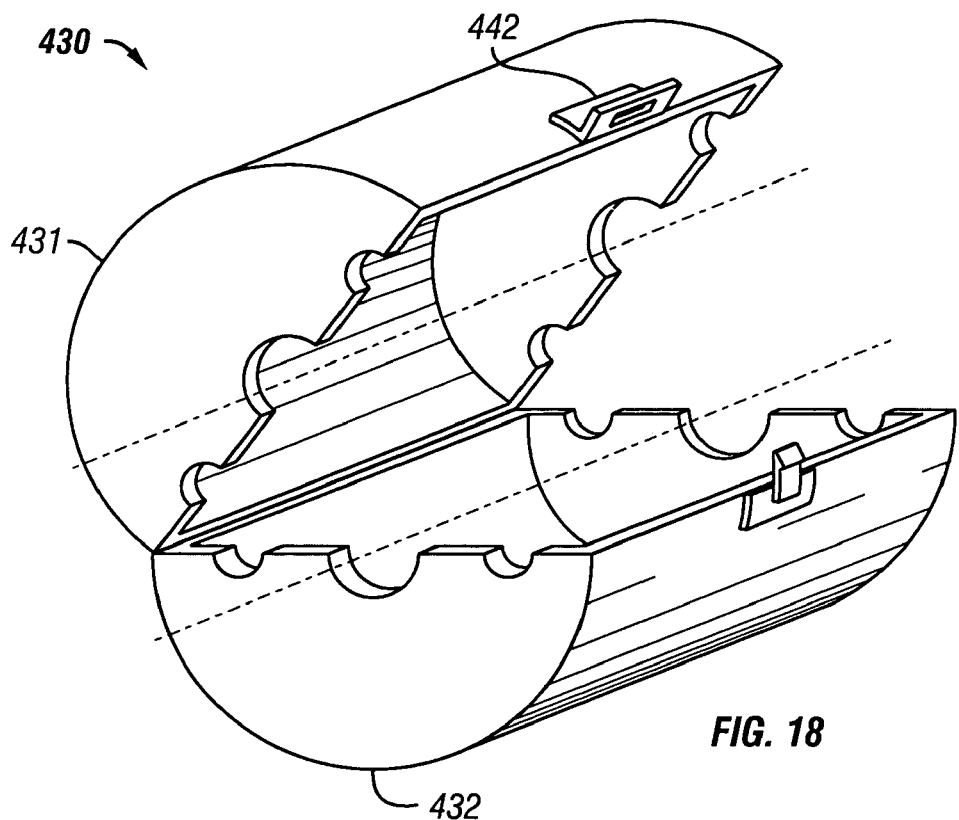
FIG. 18 shows an oblique view of the front and side of one embodiment of the bioreactor bag housing.
Figure 19:
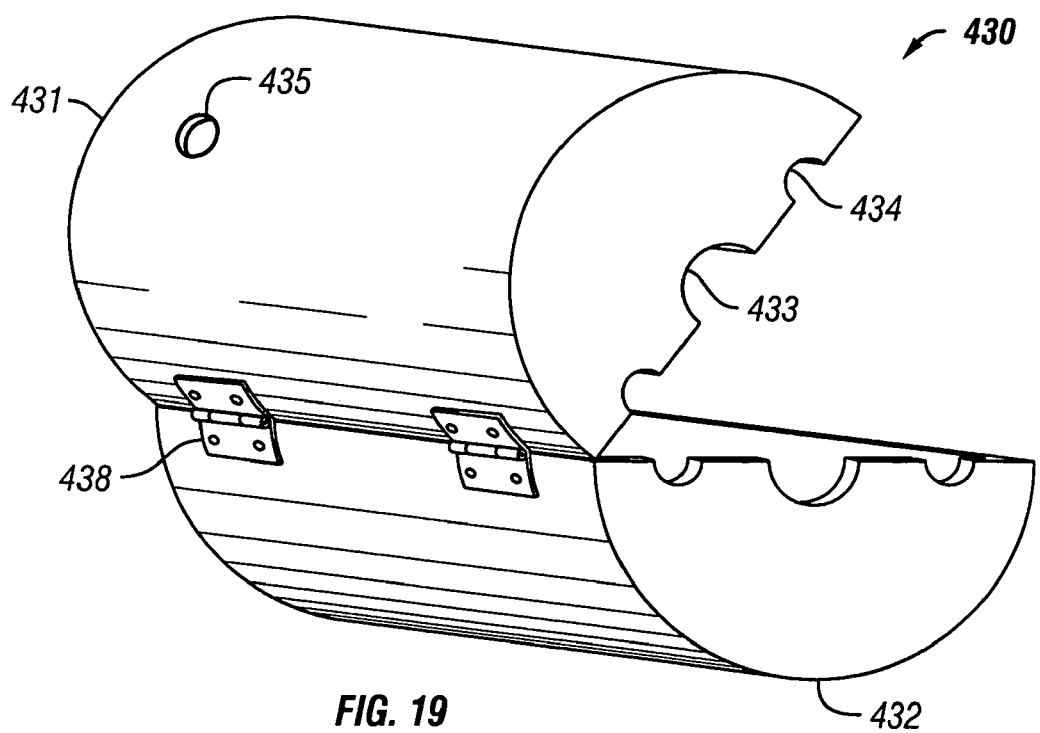
FIG. 19 shows an oblique view of the back and side of the bioreactor bag housing shown in FIG. 18.

Although the bag support housing 430 may be made any shape, the bag support housing is preferably a circular cylinder to ease its horizontal rotation. Bag support assembly 430, as shown in detail in FIGS. 18 and 19, has the external shape of a right circular cylinder and is hollow so that it has a uniform wall thickness. Bag support housing 430 has a diametrical split so that it is divided into a top portion 431 and a bottom portion 432, where the top and bottom portions are hinged together on one cylindrical side of the diametrical split and a latch 442 is provided on the opposed side of the diametrical split. The hinge 438 allows the top portion 431 and the bottom portion 432 of the bag support assembly 430 to open and close.

Central concentric bores 433 in both the transverse inlet and outlet bulkhead ends of the bag support assembly 430 are designed to fit around the bag ends 405, while additional bores 434 are located on the diametrical split so that they can readily accommodate insertion of fill ports 423 into the split bore. One or more additional radial ports 435 with clearance to permit insertion of a corresponding number of gas removal ports 425 are appropriately positioned in the cylindrical walls of the upper 431 and lower 432 portions of the bag support housing 430. The positioning of the radial ports 435 need not be on the diametrical split of the bag support assembly 430.

One advantage of bag support housing 430 is that a bag assembly 401 made with an inlet and outlet system incorporated into the bag assembly 401 can be inserted into the bag support housing 430 without having to disconnect any tubing or connectors. The bag support housing 430 may be constructed of a variety of materials known in the art, but will preferably be constructed of either a metal, such as stainless steel, or a solid plastic, such as Plexiglas™ or acrylic. A drive assembly, such as drive assembly 360 described above, horizontally rotates the bag support assembly 430.

Figure 15:
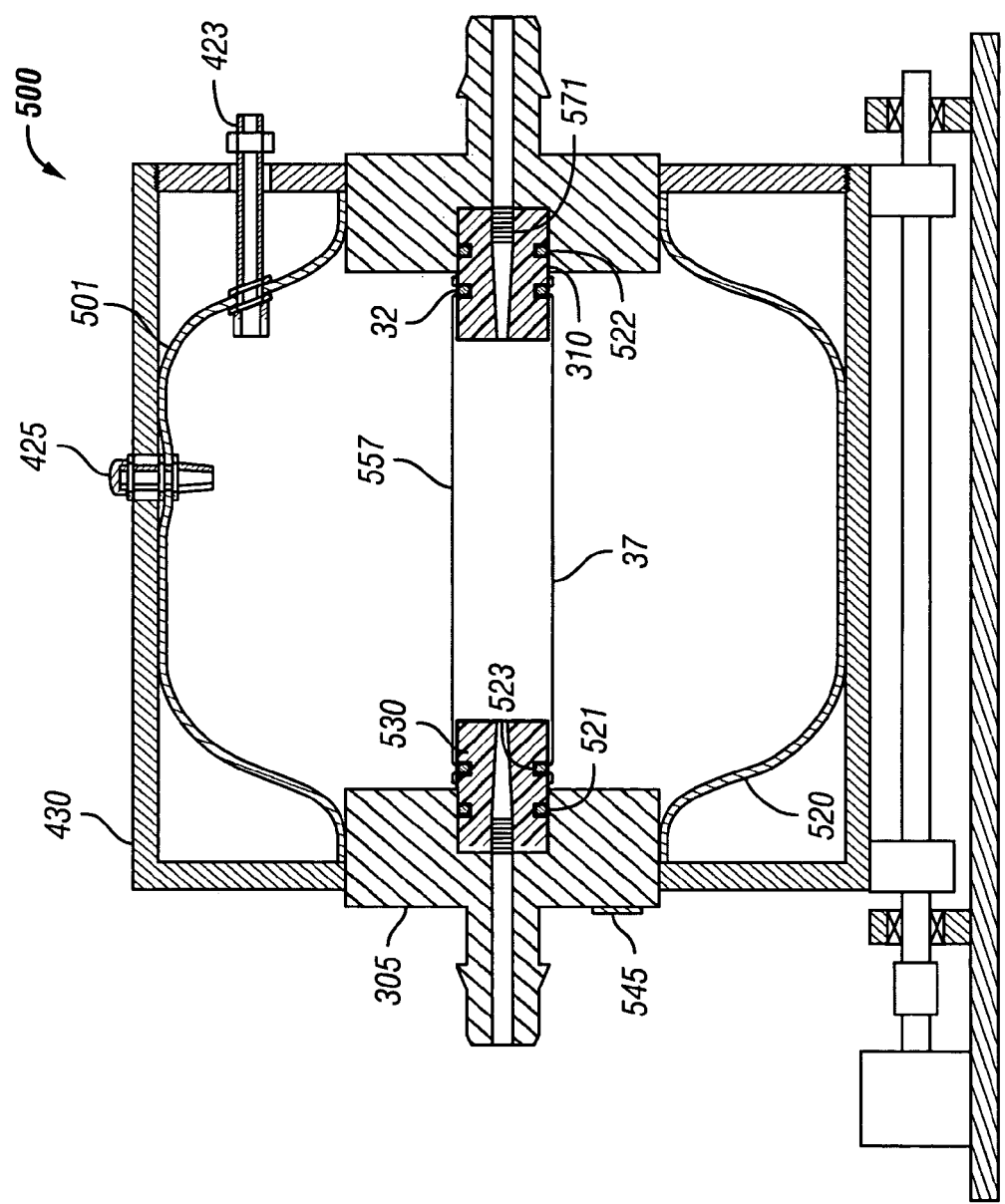
FIG. 15 shows a longitudinal cross-sectional view of another embodiment of the present invention similar to that shown in FIG. 14, but having an array of membrane carrier assemblies.

A third embodiment of the culture chamber 500 adapted for use with a disposable bioreactor bag 501 is shown in FIG. 15. The bag assembly 501 includes bag 520 and two end pieces 305 for establishing fluid interconnections and positioning the bag assembly 501. The bag 520 and 320 are alike. The end pieces 305, the vent ports 425, and fill ports 423 are alike in the bag assemblies 501 and 301. The only difference between culture chamber 300 and 500 is that bag assembly 501 of the culture chamber 500 mounts the molecular weight cut-off membrane 37 in a different manner than culture chamber 300.

As seen in FIG. 15, the diffuser assembly 557 used in culture chamber 500 is arranged similarly to the diffuser assembly 227 illustrated in FIG. 12. In fact, the diffuser assembly 227 would fit in the bag assembly 501 as well as the diffuser assembly 557. The diffuser assembly 557 uses two separate end plugs 530 which mount the molecular weight cut-off membrane 37 suspended between them.

End plug 530 is a right circular cylinder with concentric through hole 571 extending through its length. The exterior of end plug 530 has, from its outer end, male O-ring groove 521, and rectangular profile retention groove 523. O-ring 522 is mounted in groove 521.

The tubular molecular weight cut-off membrane 37 used in culture chamber 500 is identical in its shape and size to that used in the other configurations of the culture chamber. Membrane 37 is stretched over the interior end of end plug 530 past groove 522 and then sealingly retained on plug 530 by using O-ring 32 to force the membrane tightly into groove 523. One end plug 270 with its O-rings 522 and 32 is used on each end of the membrane 37 to complete the assembly of the diffuser assembly 557.

To construct cell culture chamber 500, the assembled diffuser assembly 557 has one end inserted sealingly into its corresponding flat-bottomed counterbore 310 in end piece 305 until it bottoms out. The other end of the diffuser assembly 557 is then aligned with the other end piece 305 and the end plug 530 inserted into its corresponding counterbore 310 until it bottoms out. The sides of the bag 520 are then fused to the two end pieces 305 to seal the bag assembly 501. Once the bag assembly 501 is sealed it is sterilized, preferably by gamma-radiation or gas.

Operation of the Invention

Each of the culture chambers of the present invention operate in substantially similar manners. In each case, the chamber initially is empty and must be filled with suitable biological media containing the desired cells, tissues, or other biologicals. The media is conditioned before it is pumped into the growth chamber or bag assembly. Conditioned media has a particular pH and has been gassed to contain desired quantities of oxygen and/or other gases in solution. Preferably, the culture chamber is totally filled with media and has zero headspace.

Before the media is introduced into the growth chambers of the culture chambers 10, 100, 300 and 400, the space between the membrane support cylinder 28 and the membrane 37 is filled with media. Filling the space between the support cylinder 28 and the membrane 37 is accomplished by attaching a syringe to the effluent end of the culture chamber via a luer lock valve and drawing media into the tubing and through the surface pockets 36 to form a sheet of fluid between the cylinder 28 and the membrane 37. A pump can then be used to maintain the fluid pressure within the space between the cylinder 28 and the membrane 37, while the rest of the chamber is filled with media and cells via the fill ports in the walls of the chamber.

Figure 16:
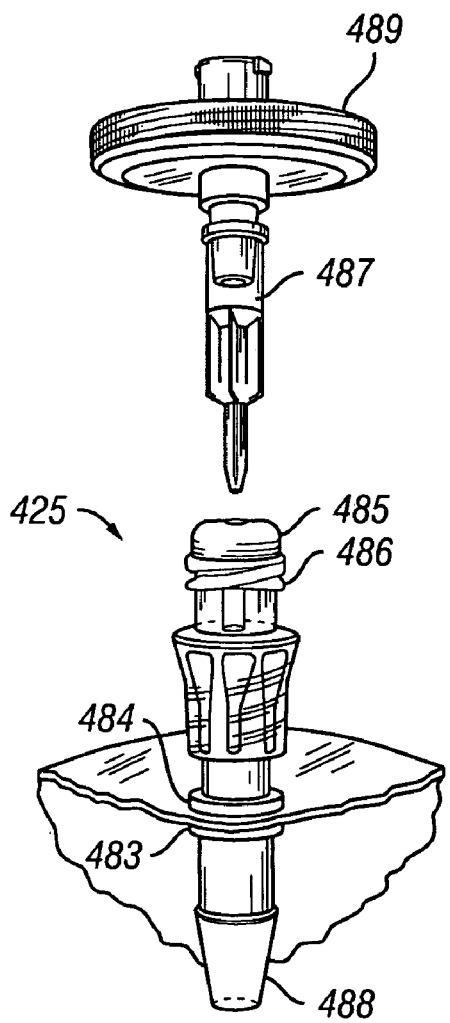
FIG. 16 shows a side view of one embodiment of a gas removal port.

To assist in filling the culture chamber 10, 100, 200, 300, 400, or 500 with media, one or more gas removal means or fill means are incorporated into the chamber assembly. As media is pumped into the chamber, gas will be displaced and must have a release mechanism. There are a variety of means known in the art for releasing gas from media storage bags as the bags are filled with media. Similar gas releasing means will work in the present invention. A preferred embodiment of a gas releasing means is the gas removal port 425, shown in FIG. 16.

The gas removal port 425 transverses both sides of the wall of the culture chamber and is sealingly attached to the wall of the chamber or bioreactor bag, be the chamber a hard walled tube such as sleeve 24 of culture chamber 10 as shown in FIG. 1 or, alternatively, a disposable bag 420 for culture chamber 400 as shown in FIG. 14. Preferably both an internal gasket 483 and an external gasket 484 are utilized to ensure that there is no leakage around the gas removal port 425 where it protrudes through the chamber wall. The internal portion 488 of the gas removal port 425 is open to the interior of the chamber. The exterior section of the gas removal port 425 has a septum 485 and a luer lock coupler 486.

To release gas from the interior of the chamber, the needle of a syringe may be inserted through the septum and the gas released through the syringe. However, a more efficient means, shown in FIG. 16, uses a fitting 487 having a sharp end to pierce the septum 485 and a coupling end to couple with an enclosed filter 489. Thus, when the fitting is inserted through the septum 485, any gas in the interior of the chamber can freely transverse the interior of the fitting and pass through the filter 489. This gas releasing means allows large quantities of gas to be removed from the chamber in a sterile manner while the chamber is being filled with media. This gas releasing means also allows the chamber to be filled with media absent air bubbles that can cause unwanted turbulence as the chamber is rotated. Furthermore, the filter 489 (preferably having about a 0.2 micron or less pore size) will prevent any contamination of the media in the event there is any back flow of air from the outside through the filter 489 into the chamber. In addition, once the fitting 487 has been removed, the septum 485 will reseal and provide an airtight seal.

The chamber will also typically have an introduction means or fill port 423 whereby media, cells, tissues, etc. can be introduced into the interior of the chamber. There are numerous means known in the art by which the chamber may be filled. In fact, the gas removal port 425 described above, can be used to introduce small quantities of media or cells into the chamber. Typically a syringe would be used to inject such materials into the chamber through the septum 485. However, for rapidly filling the chamber or introducing certain tissue or organoid materials, a larger port may be desired.

Figure 17:
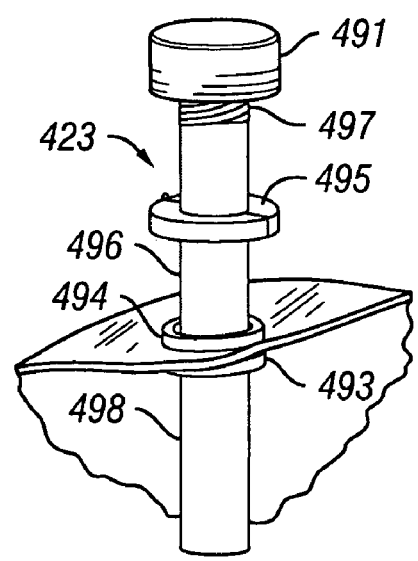
FIG. 17 shows a side view of one embodiment of a fill port.

One embodiment of a rapid fill media port such as port 423 shown for embodiment 400 in FIG. 14, is illustrated in FIG. 17. The port 423 transverses both sides of the bag 420 and is fused to the bag 420 in a similar manner as gas removal port 425. Preferably an internal gasket 493 and an external gasket 494 are utilized to ensure that there is no leakage around the rapid fill port 423 where it protrudes through the bag 420. The internal section 498 of the fill port 423 is open to the interior of the bag 420. The exterior section of the fill port 423 has a length of tubing 496 that can be opened or closed. Different closing mechanisms are available such as a pinch clamp to close off the end of the tubing when the source of media is removed, or preferably there is an end coupler that allows the end of the tubing to be capped. For example, the end coupler 495, shown in FIG. 17, has a leur lock coupler 497 for engaging a cap 491.

The stretched membrane 37 over the cylinder 28 permits development of a thin sheet of media to flow between the outer cylindrical surface of support cylinder 28 and membrane 37. Two-way perfusion through membrane 37 then permits nutrients to enter the bioreactive media inside the chamber, while waste products perfuse in the other direction into the sheet flow between cylinder 28 and membrane 37. Cells and larger sized molecules within the media in the chamber will not pass through the membrane 37 and concentrate within the chamber.

As shown in FIGS. 13-15, the transverse outer face of outlet end piece 305 and 405 are provided with a unique patient identifier 545, such as a bar code, by which the bag and its contents can be traced through processing. As may be readily understood, the patient identifier 545 may be placed at other suitable locations on the bag assembly 301, 401 and 501.

Although the present invention and its advantages have been described in detail, it should be understood that various changes, substitutions and alterations can be made herein without departing from the spirit and scope of the invention as defined by the appended claims.

What is claimed is:

1. A culture chamber comprising:
   (a) a tubular housing, wherein the housing comprises a right circular cylindrical sleeve having a first and a second end, and
   a first and a second end fitting including
   an interior projection, the interior projection having an outer diameter that sealingly fits within a bore of the sleeve,
   a nozzle on an exterior side of the end fitting,
   a counterbore in the interior projection, and
   a through bore passing through the end fitting, the through bore extending from the nozzle to the counterbore;
   (b) a growth compartment within the housing;
   (c) a liquid circulation system for circulating a culture medium through the growth compartment, the circulation system including a liquid inlet and a liquid outlet; and
   (d) a plurality of membrane carrier assembly assemblies transversing the growth compartment, wherein each membrane carrier assembly comprises
   a support cylinder having a first end in communication with the liquid inlet and a second end in communication with the liquid outlet, wherein the support cylinder transverses the growth compartment and wherein the support cylinder has an axial blind hole in the first and second end of the cylinder, the blind hole aligned with the through bore of the end fitting when the cylinder is positioned in the counterbore of the end fitting and wherein an interior end of the blind hole intersects a plurality of radial cross holes extending to the exterior surface of the cylinder,
   a molecular weight cut-off membrane secured to an exterior surface of the support cylinder, and
   a chamber bordered on one side by the exterior surface of the cylinder and on an opposed side by an interior surface of the membrane, the chamber containing circulating culture medium, wherein the membrane allows the diffusion of a set of biochemicals having a defined molecular weight between the growth compartment and the chamber.

2. The culture chamber of claim 1, wherein the plurality of radial cross holes are coplanar and equispaced about the exterior surface of the cylinder.

3. The culture chamber of claim 1, wherein each radial cross hole intersects a surface pocket on the exterior surface of the cylinder.

4. The culture chamber of claim 3, wherein the surface pocket has an arcuate cross-section.

5. The culture chamber of claim 3, wherein the surface pocket extends from a point of intersection with the radial cross hole to a termination point on the exterior surface of the cylinder, the termination point positioned between the point of intersection and a mid-point of a length of the cylinder.

6. A culture vessel comprising:
   (a) a housing having
      a right circular cylindrical sleeve having a first and a second end; and
      a first and a second end fitting including an interior projection, the interior projection having an outer diameter that sealingly fits within a bore of the sleeve to seal the first and second ends of the sleeve,
      a nozzle on an exterior side of the first and second end fitting,
      a counterbore in the interior projection, and
      a through bore passing through the first and second end fitting, the through bore extending from the nozzle to the counterbore;
   (b) a growth compartment within the bore of the sleeve;
   (c) a support cylinder transversing the growth compartment, the support cylinder having a first and second end, each end having a liquid channel extending from the end of the cylinder to an exterior surface of the cylinder, wherein the liquid channel includes a blind hole in the end of the cylinder that intersects a plurality of coplanar radial cross holes extending to the exterior surface of the cylinder, and a plurality of surface pockets intersected by the radial cross holes, whereby the liquid channel is in liquid communication with the through bore of the end fitting whenever the cylinder is positioned in the counterbore of the interior projection; and
   (d) a molecular weight cut-off membrane secured to an exterior surface of the support cylinder and overlaying the surface pockets in the exterior surface of the cylinder to provide a chamber between the exterior surface of the cylinder and an interior surface of the membrane, the chamber in liquid communication with the liquid channels of the support cylinder and the growth compartment, wherein the membrane allows the passage of a set of biochemicals having a defined molecular weight between the growth compartment and the chamber.

7. The culture chamber of claim 6 having a number of chambers transversing the growth compartment, wherein each chamber is a component of a liquid circulation system for circulating a liquid culture medium through the growth compartment.

8. A culture chamber comprising:
   (a) a tubular housing;
   (b) a growth compartment within the housing;
   (c) a liquid circulation system for circulating a culture medium through the growth compartment, the circulation system including a liquid inlet and a liquid outlet;
   (d) a plurality of membrane carrier assemblies transversing the growth compartment, each membrane carrier assembly comprising
      (i) a support cylinder having a first end and a second end, each end having a fluid channel comprising
         a blind hole in the end of the cylinder,
         a plurality of coplanar radial cross holes extending from the blind hole to the exterior surface of the cylinder, and
         a surface pocket on the exterior surface of the cylinder, wherein each surface pocket is intersected by one cross hole, and
      (ii) a molecular weight cut-off membrane secured to an exterior surface of the support cylinder over the surface pockets of the fluid channels, wherein the membrane defines a set of biochemicals in the circulating culture medium for which passage through the membrane is restricted, and
      (iii) a chamber between the exterior surface of the cylinder and an interior surface of the membrane, the chamber in fluid communication with the liquid inlet and the liquid outlet.

* * * * *